United States Patent [19]
Kittrell et al.

[11] Patent Number: 5,562,100
[45] Date of Patent: Oct. 8, 1996

[54] METHOD FOR LASER INDUCED FLUORESCENCE OF TISSUE

[75] Inventors: Carter Kittrell, Houston, Tex.; Robert M. Cothren, Cleveland Hts., Ohio; Michael S. Feld, Waban, Mass.; Joseph J. Baraga, Hibbing, Minn.; Kyungwon An, Seoul, Rep. of Korea; Rebecca Richards-Kortum, Cambridge; Richard P. Rava, Boston; Young D. Park, Acton; Anand V. Mehta, Cambridge, all of Mass.; Paola Taroni, Como, Italy; Lucene Tong, Hayward, Calif.; Ramachandra R. Dasari, Lexington, Mass.

[73] Assignee: Massachusetts Institute of Technology, Cambridge, Mass.

[21] Appl. No.: 249,086

[22] Filed: May 25, 1994

Related U.S. Application Data

[63] Continuation of Ser. No. 82,342, Jun. 24, 1993, abandoned, which is a continuation of Ser. No. 920,151, Jul. 27, 1992, abandoned, which is a continuation of Ser. No. 288,772, Dec. 21, 1988, abandoned.

[51] Int. Cl.$^6$ ...................................................... A61B 5/00
[52] U.S. Cl. .................................................................. 128/665
[58] Field of Search .............................. 128/633-4, 664-5

[56] References Cited

U.S. PATENT DOCUMENTS

| Re. 31,815 | 1/1985 | Alfano . | |
|---|---|---|---|
| 4,162,405 | 7/1979 | Chance et al. . | |
| 4,178,917 | 12/1979 | Shapiro | 128/633 |
| 4,236,526 | 12/1980 | Richard | 128/633 |
| 4,556,057 | 12/1985 | Hiruma et al. . | |
| 4,641,650 | 2/1987 | Mok . | |
| 4,718,417 | 1/1988 | Kittrell et al. | 128/666 |
| 4,737,628 | 4/1988 | Lovoi . | |

(List continued on next page.)

FOREIGN PATENT DOCUMENTS

| 3210593 | 10/1982 | Germany . |
|---|---|---|
| 929050 | 5/1982 | U.S.S.R. . |
| 2203831 | 10/1988 | United Kingdom . |
| WO84/04665 | 12/1984 | WIPO . |
| WO88/00465 | 3/1988 | WIPO . |
| WO89/05295 | 11/1988 | WIPO . |
| WO88/03257 | 4/1989 | WIPO . |

OTHER PUBLICATIONS

P. Jansson, "Deconvolution With Application In Spectroscopy" (1984) Chapter 1, pp. 1–33, Chapter 5, pp. 136–152.

Publication of Alfan et al. (1984), IEEE vol. QE 20, No. 12, pp. 1507–1511.

Publication of Sartori et al. (1984), IEEE vol. QE–23, No. 10, pp. 1794–1797.

Publication of Kittrell et al. (1985), Laser Radiation to produce tissue fluorescence spectra.

Publication of Hoyt et al, Use of Laser induced fluorescence of tissue.

Publication of Cothren et al. (1986), Laser catheter for controlled delivery of laser radiation to tissue in vivo.

Publication of Cothren et al. (1986), Laser catheters to provide a spectral representation or map of tissue.

Publication of Montan et al. (1985), Laser induced fluorescence of tissue to aid in cancerous tissue.

Publication of Andersson et al. (1985), Laser induced fluorescence of tissue to aid in cancerous tissue.

*Primary Examiner*—Angela D. Sykes
*Attorney, Agent, or Firm*—Hamilton, Brook, Smith & Reynolds, P.C.

[57] ABSTRACT

A method for laser induced fluorescence of tissue in which laser radiation is used to illuminate and induce fluorescence in the tissue under study to determine the chemical composition or pathologic condition of tissue. The laser radiation and the retrieved fluorescing radiation can be conveyed through a catheter using an array of optical fiber. The fluorescence spectrum of the tissue can be displayed and analyzed to obtain information regarding the chemical composition and medical condition of the tissue inside the human body.

16 Claims, 16 Drawing Sheets

Normal intima

U.S. PATENT DOCUMENTS

| | | | |
|---|---|---|---|
| 4,957,114 | 9/1990 | Zeng et al. | 128/665 |
| 4,981,138 | 1/1991 | Deckelbaum et al. | 128/665 |
| 5,042,494 | 8/1991 | Alfano | 128/665 |
| 5,046,501 | 9/1991 | Crilley | 128/665 |
| 5,062,431 | 11/1991 | Potter | 128/665 |

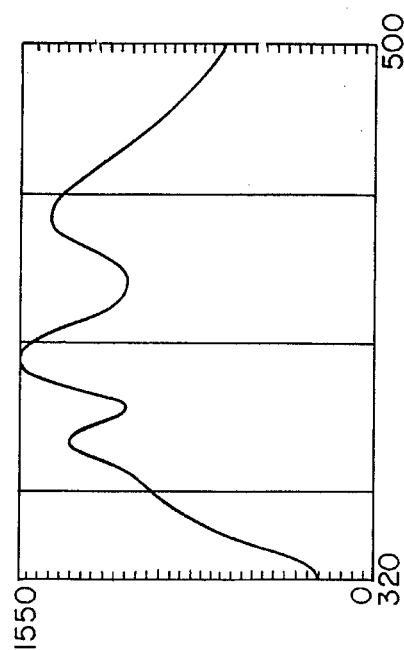
Fig. 1A Normal intima
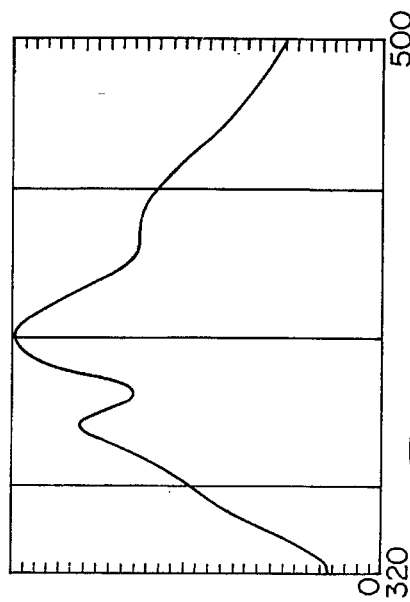
Fig. 1B Fiberous plaque
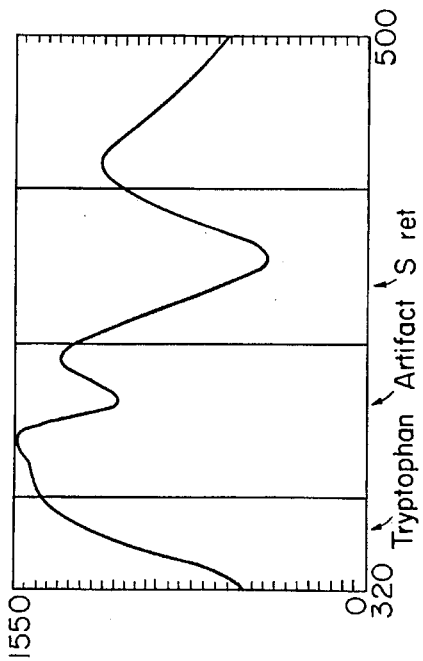
Fig. 1C Fatty plaque
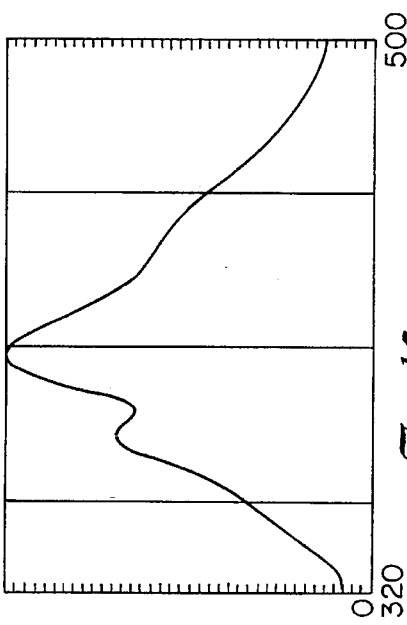
Fig. 1D Calcified plaque

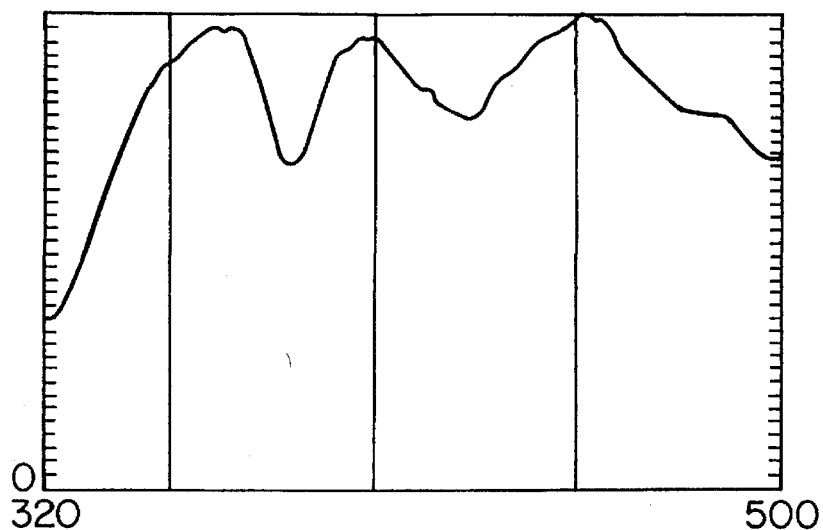
Fig. 2A  Normal: ablated into, but not through, normal media
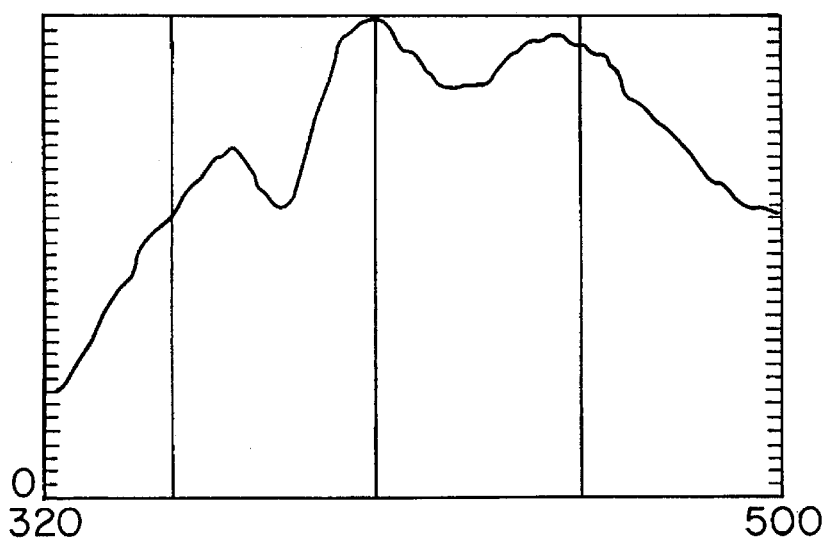
Fig. 2B  Plaque: ablated into, but not through, normal media

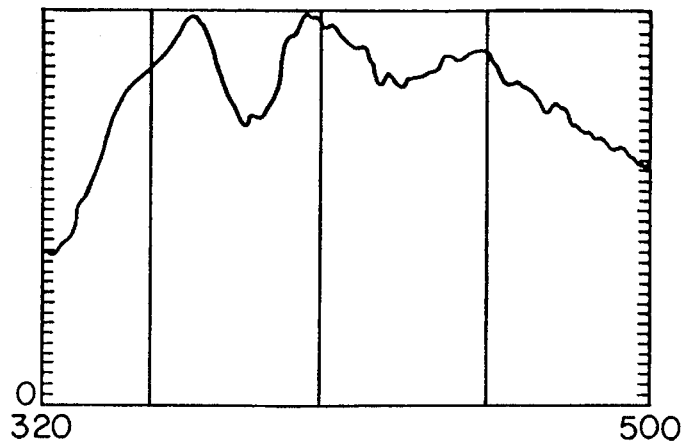
Fig. 2C Plaque/normal: ablated through plaque into media
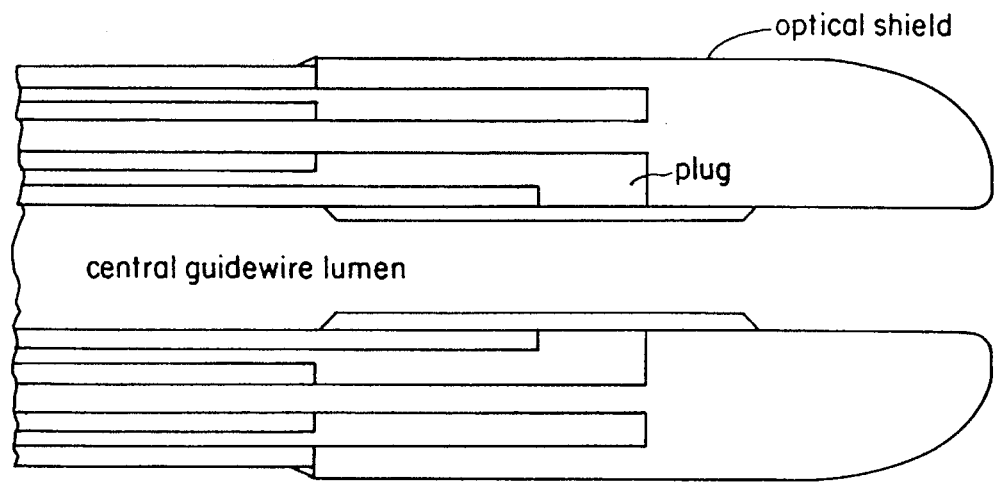
Fig. 3A
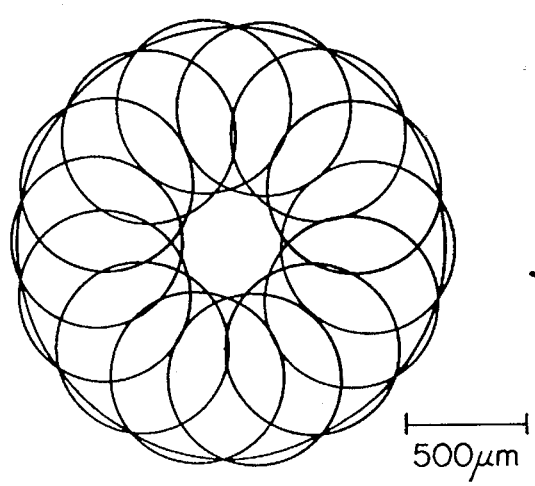
Fig. 3B

Normal Tissue

Fibrous Plaque

Fatty Plaque

METHOD FOR LASER INDUCED FLUORESCENCE OF TISSUE

GOVERNMENT SUPPORT

This invention was made with government support under Grant Number NIH-5-P41-RR02594 awarded by the National Institutes of Health. The government has certain rights in the invention.

This application is a continuation of application Ser. No. 08/082,342, filed Jun. 24, 1993, now abandoned, which is a File Wrapper Continuation of U.S. Ser. No. 07/920,151, filed Jul. 27, 1992, now abandoned, which is a File Wrapper Continuation of U.S. Ser. No. 07/288,772, field Dec. 21, 1988, now abandoned.

BACKGROUND OF THE INVENTION

The present invention relates to optical and laser spectroscopy and, in particular, laser induced fluorescence (LIF) spectroscopy which has recently been explored as a technique for medical diagnosis.

It has been shown that fluorescence spectroscopy can be used to diagnose the presence of atherosclerosis in human artery wall, emphasizing the use of empirically defined algorithms to determine tissue type from fluorescence spectra. For example, using 476 nm LIF spectroscopy, Kittrell et al., "Diagnosis of Fibrous Atherosclerosis Using Fluorescence", *Applied Optics* 24, 2280 (1985), has demonstrated that such an empirical algorithm could be used to differentiate normal aorta and early atherosclerotic plaque in vitro. Fluorescence spectra of normal aorta and fibrous plaque were differentiated by the peak to valley ratio of the fluorescence intensity at ca. 600 nm to that at 580 nm.

Catheters employing optical fibers for the illumination, viewing and treatment of tissue are now used with sources of laser radiation for a variety of medical applications. Through the insertion of the catheter into a human artery or bodily cavity, laser radiation of a given wavelength can be used to illuminate tissue within the body such that the tissue fluoresces. Radiation generated by tissue fluorescence is then conveyed by one or more of the optical fibers to the proximal end of the catheter where it can be analyzed to yield information about the tissue under examination.

SUMMARY OF THE INVENTION

The method of the present invention relates to the diagnosis of tissue by targeting chromophores in the tissue with optical radiation and analyzing returning radiation to determine type and abundance of chromophores and, hence, utilizing laser induced fluorescence of chromophores contained in the tissue. The method provides a technique for rapid identification and diagnosis of tissue without highly invasive procedures previously in use.

Chromophores that naturally occur in tissue respond to incident light by several processes. Absorption of light by the tissue will occur based on the characteristics of each of the chromophores that are present. Single or multiple wavelength excitation will provide a characteristic spectrum or profile of the tissue being illuminated. Some of the chromophores in the tissue will fluoresce depending upon the excitation wavelength or wavelengths so that the fluorescence emission will define a characteristic profile for that tissue.

Note that the emission also has a fluorescence lifetime which may be measured and analyzed to reveal important diagnostic information. In addition, the chemical moieties in the tissue exhibit inelastic or Raman scattering, which also provides useful spectral information.

The total spectrum is the sum of the individual contributions of the many chemical constituents of the tissue. When additional excitation wavelengths are used, chromophore excitation is also altered, some emitting at stronger intensities and some weaker. The overall profile changes as each individual contribution changes. The use of many excitation wavelengths assists in the identification of the chromophores present in the tissue.

In particular, tuning through the absorption edge of a chromophore can result in sharp changes in the emission spectrum. Tuning close to the edge allows the spectral profile to be adjusted like a dimmer switch relative to the other chromophore contributions to the spectrum.

Since different types of tissue have different chemical composition, spectroscopy can be used to identify different chromophores present in the tissue being diagnosed. By measuring in the tissue the presence and amount of the chromophores present the tissue type can be more fully characterized. For increased accuracy in diagnosis, or to help distinguish between similar but non-identical tissues, several wavelengths may be used to target several chromophores.

Excitation of naturally occurring chromophores with ultraviolet light in the 305–310 nm range generates fluorescence spectra (330–500 nm) which are useful in characterizing tissue type and condition. Various types of arterial tissue, including normal, diseased aorta and coronary artery have been examined to obtain spectra in bulk tissue using conventional collection optics.

In vivo applications utilize a catheter containing one or more optical fibers which is inserted into an artery, bodily cavity or tissue surface such that the distal end is positioned adjacent to the tissue to be diagnosed. A specific chromophore or group of chromophores is then selected for analysis by selecting an irradiating wavelength known to excite such chromophore or group of chromophores. A source of optical or laser radiation is then coupled to the proximal end of selected fibers within the catheter and the tissue being analyzed is then illuminated with radiation, causing it to fluoresce. The scattered fluorescent light from the tissue is then transmitted along the fibers to the proximal end of the catheter, where it is analyzed to determine the chromophores and, hence, diagnose the tissue.

The laser wavelength can be tuned to match the peak absorption of the chromophore being detected. Alternatively the wavelength or wavelengths can be selected to discriminate between adjacent peaks of known chromophores. It may be tuned to the absorption edge. Other characteristics of the tissue can be ascertained by exciting two chromophores and determining the ratio of the fluorescence peaks.

This present method provides information regarding the chemical constituents of the tissue being examined. In particular, the presence of certain fluorophores can be detected whose presence is an indicator of specific tissue pathology. Tissue fluorescence spectra can be deconvolved to yield more information regarding the fluorescence spectra.

A further embodiment of the present invention relates to a method of tissue analysis involving the use of time-decay laser induced fluorescence spectroscopy. The monitoring of fluorescence decay times also provides information regarding the chromophores present in human tissue.

Human aortic tissue and coronary artery tissue has been excited in the range of 305–312 nm to produce fluorescence decay signals in the range of 320 nm to 500 nm. This has provided information regarding the presence of certain fluorophores in the tissue, including the contribution thereof to the spectral lineshape.

Note that these procedures are performed on endogeneous tissue, that is, tissue that has not been treated with dyes or stains commonly used to enhance the fluorescence characteristics of biological materials or tissue. The present method thus provides for the rapid diagnosis of "native" or endogeneous tissue, including tissue within human subjects accessed by catheters having optical fibers to couple precisely controlled amounts of radiation to the tissue.

The above, and other features of the invention including various novel details of construction and combination of parts, will now be more particularly described with reference to the accompanying drawings and pointed out in the claims. It will be understood that the particular method of laser induced fluorescence of tissue embodying the invention is shown by way of illustration only and not as a limitation of the invention. The principal features of this invention may be employed in various embodiments without departing from the scope of the invention.

BRIEF DESCRIPTION OF THE DRAWINGS

FIGS. 1A, 1B, 1C and 1D are graphical illustrations of emission spectra resulting from a 310 nm excitation wavelength of normal intima (1A), fibrous plaque (1B), fatty plaque (1C) and calcified plaque (1D) where the typical pulse energy is 150 nJ.

FIGS. 2A, 2B and 2C are graphical illustrations of emission spectra of ablation damaged tissue excited at a 305 nm wavelength. FIG. 2A shows the emission spectrum of normal tissue after ablation into but not through the tissue. FIG. 2B shows the emission spectrum after ablation into, but not through fatty plaque. FIG. 2C shows the emission spectrum of tissue after ablation rough plaque into normal tissue.

FIGS. 3A and 3B illustrate cross-sectional and end views of the distal end of a preferred embodiment of a catheter that is used with the invention where FIG. 3B further illustrates a pattern of overlapping light spots on the distal surface of the optical shield.

DETAILED DESCRIPTION

Excitation of naturally occurring chromophores with ultraviolet light in the 305–310 range generates fluorescence spectra (330–500 nm which are useful in characterizing tissue type and condition. Various types of arterial tissue, including normal and diseased aorta and coronary artery have been examined to obtain spectra in bulk tissue using conventional collection optics.

In all cases, the excitation source for the Laser Induced Fluorescence (LIF) was a dye laser pumped by a 10 Hertz Nd:YAG laser and frequency doubled. Gated integration minimized background noise by taking advantage of the ten nsec duration pulse. The results show that the tissue LIF has several spectral features which vary with tissue type and condition.

The spectra taken in bulk tissue indicate that normal aorta can be distinguished from plaque, and that different types of plaque (fibrous, fatty and calcified) show different emission spectra (FIG. 1). The tissue tolerance to the low power diagnostic ultraviolet light is good. Even after substantial exposure, distinctive spectral features remain even though there is a significant loss of fluorescence energy. After ablation with a high power argon-ion laser, the remaining aortic plaque can be distinguished from damaged normal media (FIG. 2). (The excitation wavelength is changed from 310 to 305 in this case). When plaque has been ablated away exposing the underlying media, the ultraviolet LIF spectrum more closely matches that of normal media which had no overlying plaque, that is, this technique determines when the plaque layer has been penetrated.

Figure 7:
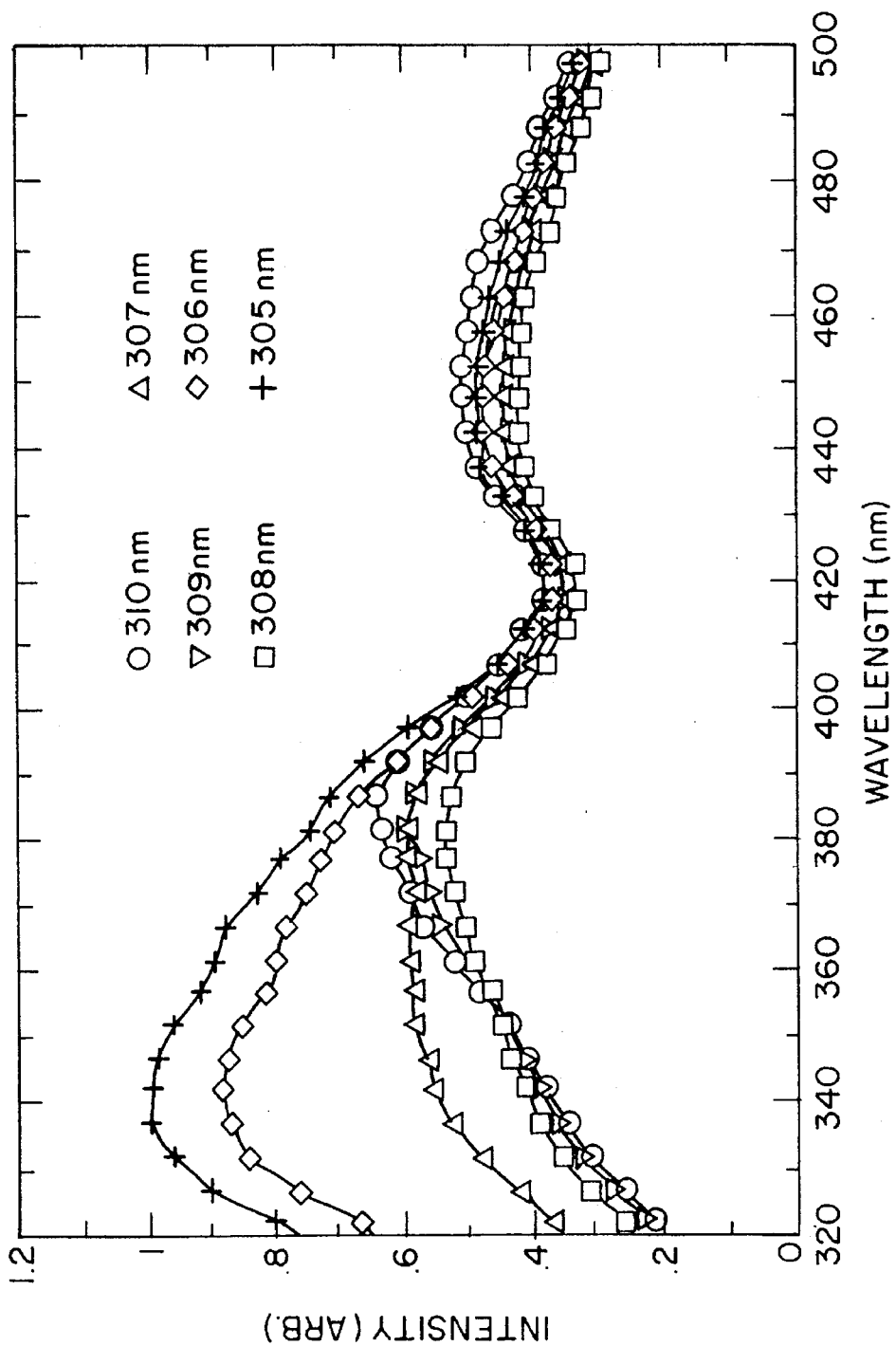
FIG. 7 is a schematic graphical illustration of the fluorescence emission intensity plotted versus wavelength for the six different excitation wavelengths 305 nm, 306 nm, 307 nm, 308 nm, 309 nm and 310 nm.

Spectral features are very sensitive to excitation wavelength; changing from 305 nm to 310 nm makes a substantial difference. Tryptophan fluoresces strongly with 285 nm excitation and dominates the spectra, but the long wavelength weak absorption "tail" occurs in the 305–310 nm range, so that a careful selection of the excitation wavelength will act as a chromophore "dimmer switch" and control the size of the tryptophan emission peak at about 340 nm. FIG. 7 shows six LIF spectra from a single sample, each taken with a different excitation wavelength ranging from 305 to 310 nm in 1 nm steps. With 310 nm excitation, the spectrum consists of two peaks at 387 nm and 450 nm, with a valley between them at 417 nm. At shorter excitation wavelengths, a new peak at 340 nm appears. This peak grows with decreasing excitation wavelength, while the 387 nm and 450 nm peaks remain relatively constant; at 305 nm excitation, the 340 nm peak dominates the spectrum. This large change in emission profile with relatively small changes in excitation wavelength suggests that at least two fluorophores are being observed. In the five samples studied, a 30% variation was observed in the ratio of fluorescence intensity at 340 nm to that at 387 nm with 308 nm excitation.

Figure 8A:
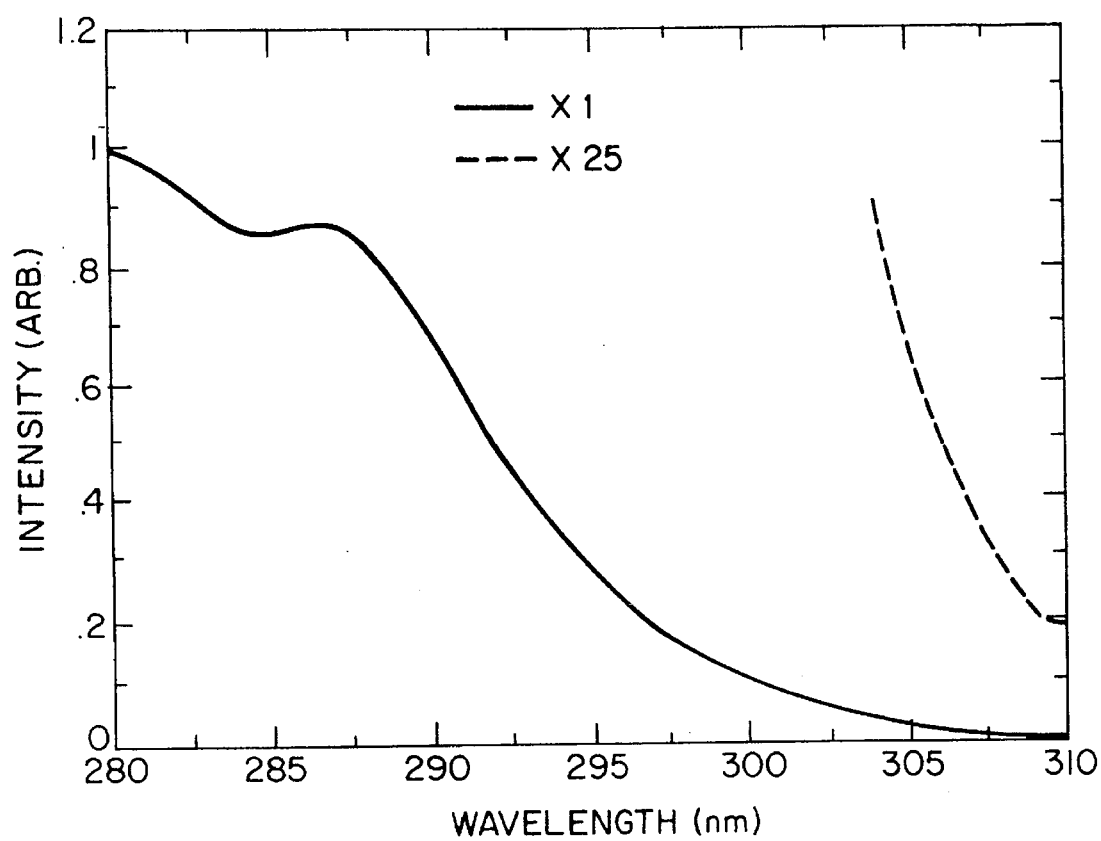
FIGS. 8A and 8B are schematic graphical illustrations plotting intensity (arbitrary units) versus wavelength of an excitation scan (7A) of L-tryptophan in tris buffer with the emission peak at 350 nm, and the emission scan (8B) with excitation at 308 nm.
Figure 8B:
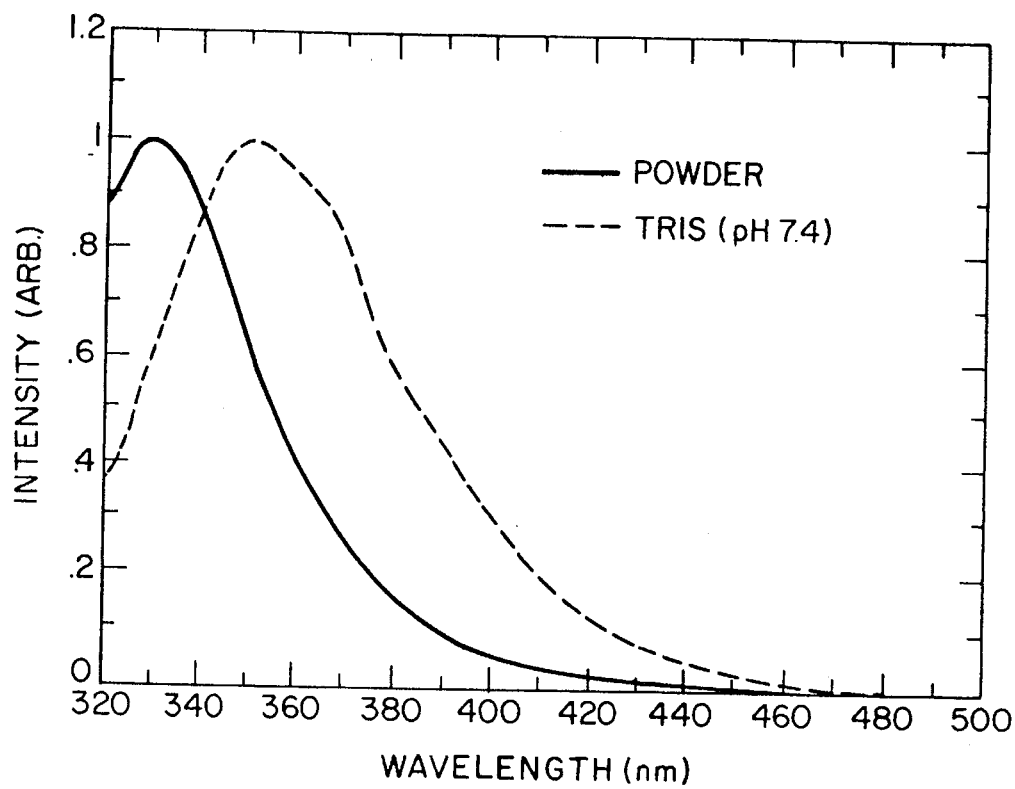

The fluorescence peak at 340 nm is attributed to tryptophan, a well-known UV fluorophore. Tryptophan in aqueous solution shows a 60 nm FWHM fluorescence band peaking at 348 nm when excited in the ultraviolet. The peak position is somewhat sensitive to environment; for instance, tryptophan powder peaks at 330 nm when excited with 308 nm. An LIF spectrum of L-tryptophan (Sigma) excited at 308 nm is shown in FIG. 8, along with an excitation spectrum of a similar solution, generated on a conventional spectrofluorimeter. FIG. 8A shows that 305–312 nm is on the long wavelength edge of exciting tryptophan, so that tuning to wavelengths shorter than 310 nm greatly enhances tryptophan fluorescence. This same behavior is observed in tissue, making tryptophan a likely candidate observed at the 340 nm.

The appearance of a peak in an emission spectrum is usually associated with a distinct fluorophore having its maximum emission at that wavelength. Although a fluorophore emitting at 450 nm cannot be ruled out, in the present spectra the 450 nm peak is probably a result of the singly-peaked broadband fluorescence at 387 nm, distinct from the fluorescence at 340 nm, modulated by reabsorption near 417 nm. It has been demonstrated that the valleys in their visible LIF spectra of arterial wall above 500 nm are due to reabsorption by oxy-hemoglobin or other porphyrin type absorbers. The Sorer absorption band of oxy-hemoglobin occurs at 415 nm, matching the wavelength of the valley in our spectra. This hypothesis was confirmed by the absence of this valley in LIF spectra of 4 μm tissue sections taken with a Leitz UV-fluorescence microscope. Such sections are essentially free of reabsorption; consequently, the absence of the 417 nm valley in the thin section indicates that the valley in our bulk tissue spectra is due to reabsorption of LIF. Similar valleys previously observed in the visible in artery and in breast tissue are likely due to the same effect.

Figure 9:
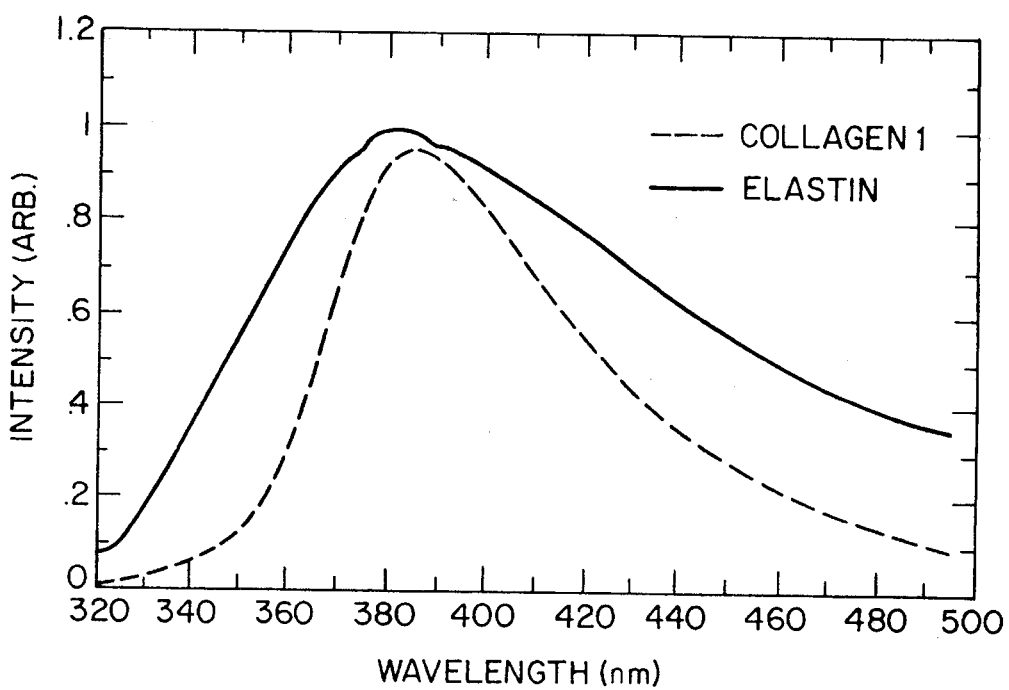
FIG. 9 is a schematic graphical illustration of emission spectra for collagen I and elastin powder at 308 nm excitation.

Additional experiments indicate that the fluorescence peak at 387 nm may be due to collagen and/or elastin. Collagen I powder, when excited at 308 nm, displays a 62 nm FWHM fluorescence band peaked at 386 nm (FIG. 9). Elastin powder fluorescence, also shown, peaks between 380 and 384 nm and is roughly 120 nm FWHM. Collagen and elastin have recently been identified as containing tissue fluorophores observed in the visible and both molecules are found in abundance in artery wall. In addition, collagen fluorescence has been observed with UV excitation and the fluorescent component pyridinoline has been identified which is a cross-linking aromatic amino acid-like compound. A similar cross-linking agent is found in elastin. These cross-links are likely to be primary contributors to the tissue fluorescence.

Figure 4:
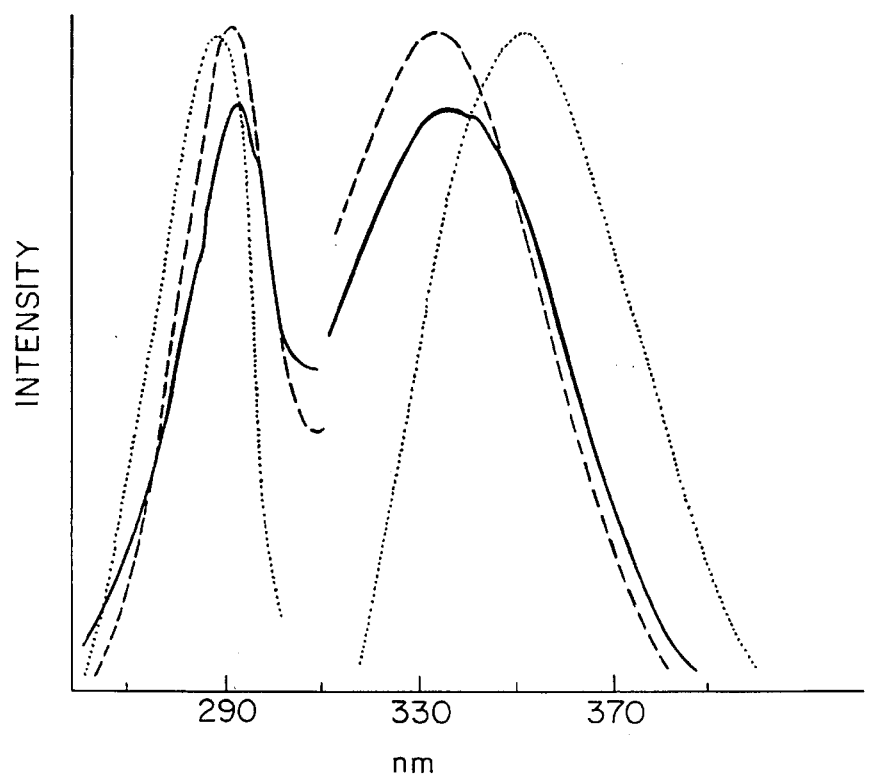
FIG. 4 graphically illustrates excitation and emission profiles of tryptophan ($10^{-5}$M) (·····), *S. epidermidis* (-----), and *E. coli* (———). The excitation scans were obtained with $\lambda_{em}$=340 nm and the emission scans were obtained with $\lambda_{ex}$=290 nm. Note that the intensity scale has been arbitrarily adjusted.
Figure 5:
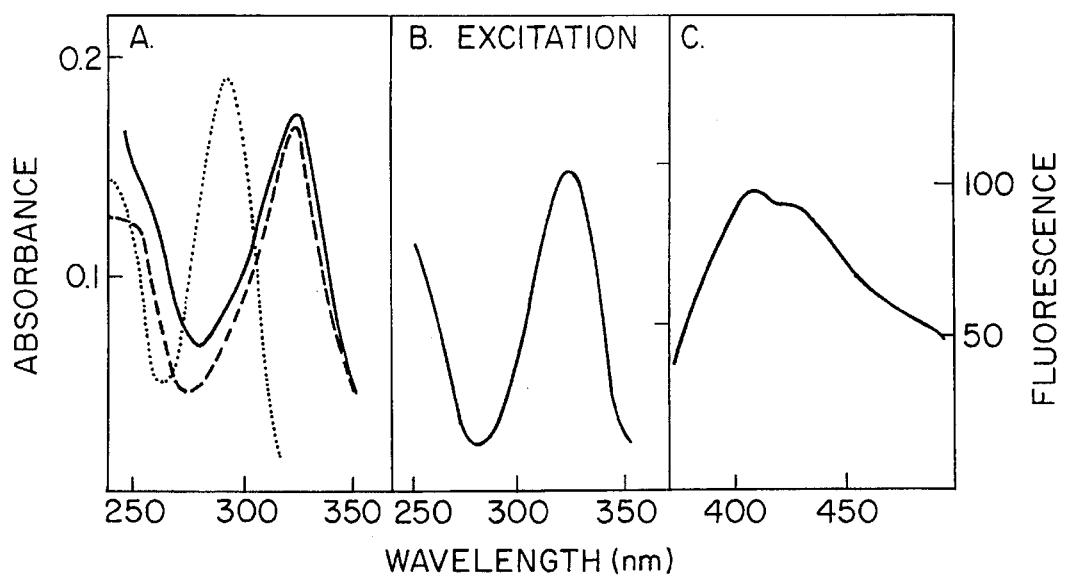
FIG. 5 includes graphical illustrations of spectra showing the UV absorption of pyridinoline in 0.1N HCl (-·-·-), in 0.1N potassium phosphate buffer, pH 7.4 (-----), and 0.1N NaOH (———) (A); the activation spectrum in 0.02M potassium phosphate buffer, pH 7.4 with fluorescence at 400 nm (B); and the fluorescence spectrum in 0.02M potassium phosphate buffer, pH 7.4, with activation at 325 nm (C).

In the above example, the excitation wavelength is on the short wavelength absorption maximum of the collagen peak, so the collagen intensity may vary in the opposite direction of tryptophan, and more slowly. Therefore, excitation wavelength may be carefully selected so that tryptophan emission is relatively strong in tissue which contains it, such as normal media; and is relatively weak in tissue with low tryptophan content, such as fatty or calcified plaque. Likewise, pyridinoline is a fluorescent compound found in elastin and collagen (FIG. 5) and is likely to contribute to the 400 nm signal which is strongest for elastic tissue. Thus, correlating observed LIF spectra to tissue composition is possible when excitation wavelengths may be selected to enhance differences based on known differences in chemical make-up of different types of tissue.

The argon ion laser tissue ablation substantially reduces the tryptophan content as the heat sensitive chromophore is degraded. This is observed as a substantial decrease in fluorescence yield with 280 nm excitation. To compensate for this, the excitation wavelength is shifted to 305 nm for studying ablation-damaged tissue (FIG. 2). The emission signal from the small amount of tryptophan remaining is enhanced, by using a shorter wavelength, and ablation-damaged plaque and media can be distinguished.

This sensitivity to excitation wavelength should also be considered when studying tissues with a high nucleic acid content. Absorption overlaps that of tryptophan, but the quantum yield is much less. However, at the tryptophan edge, there is the potential for relative enhancement of nucleic acid absorption. The emission may well contribute to the 360 nm range of the LIF tissue spectra. Narrowband excitation is very important; when searching for that wavelength, any strong shorter wavelengths eliciting a powerful response from tryptophan. As explained above, the large valley at 420 nm in the spectra of FIG. 7 is due to the absorption by hemoglobin in the tissue. This hemoglobin absorption is due to the Soret absorption band of porphyrin. This will not be caused by hemoglobin alone, as the Soret band is characteristic of porphyrins in general.

Figure 6:
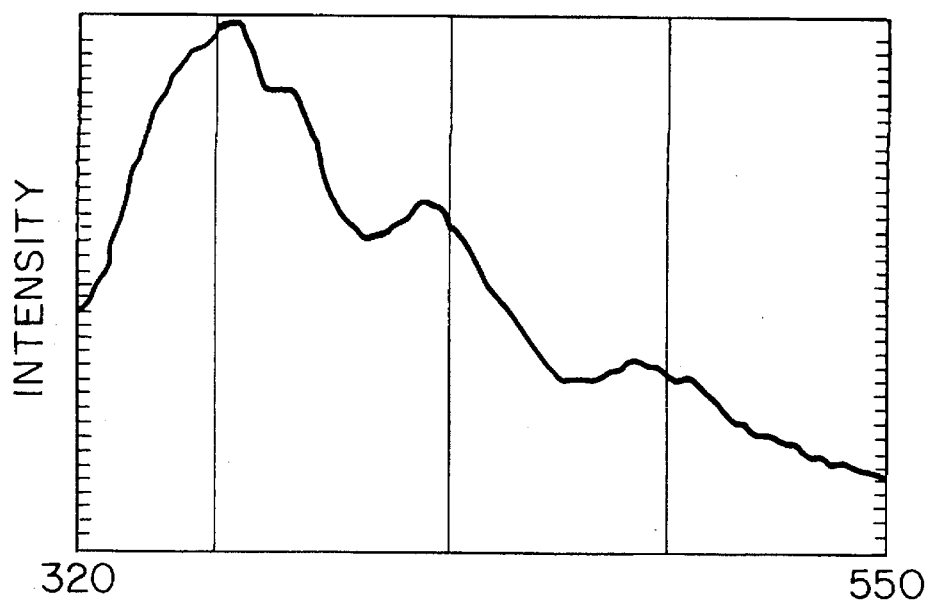
FIG. 6 is a graphical illustration of the emission spectrum of normal aortic tissue taken with a fiber-optic device with excitation at 305 nm.

Spectra were also recorded using a fiber-optic device (FIG. 6). An epoxy plug containing 200 micron core silica fiber was inserted into a 3 mm silica test tube. A central fiber illuminated the tissue and the six collector ring fibers had the proximal ends placed at the monochromator slit. One collection fiber can be separately connected to a photodiode to monitor laser pulse energy impinging on the tissue, which could be ratioed, or if coupling optics are used, the scattered laser light could be split off near the monochromator.

Time decay ultraviolet-excited LIF has been performed with the psec laser system using Time Correlated Photon Counting (TCPC). This method can determine fluorescence decay times with resolution of 30–100 psec. It is also good for poor fluorescers; being a photon counting system, it is designed to work well with weak signals. In fact, strong signals may require attenuation. The TCPC method has become well known and needs no further description.

Figure 10:
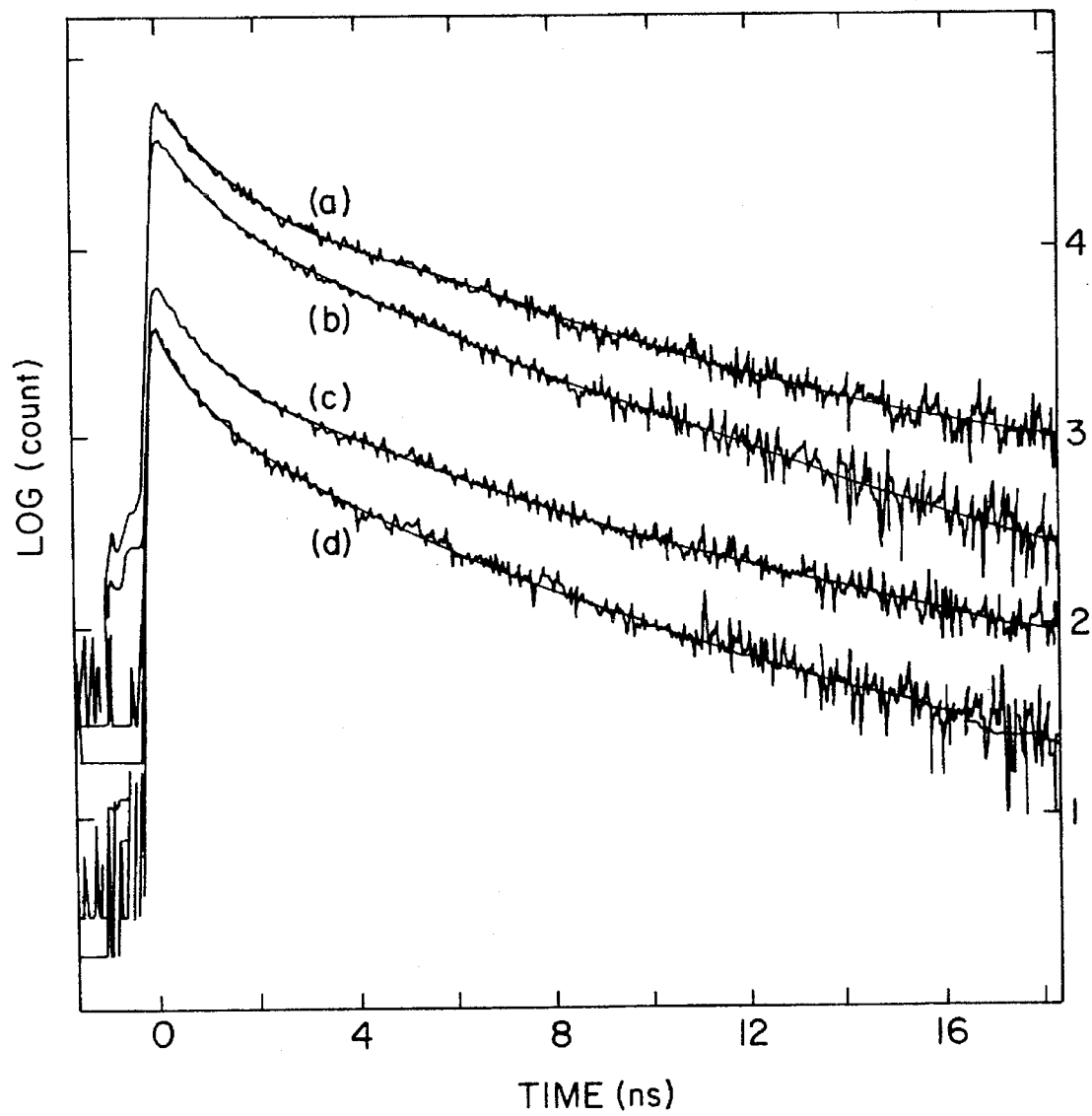
FIG. 10 is a graphical illustration plotting fluorescence decay curves of human aorta at (a) 305 nm excitation and 440 nm emission, (b) 305 nm excitation and 350 nm emission, (c) 310 nm excitation and 440 nm emission and (d) 310 nm excitation and 350 nm emission. The curves have been offset relative to one another.
Figure 11:
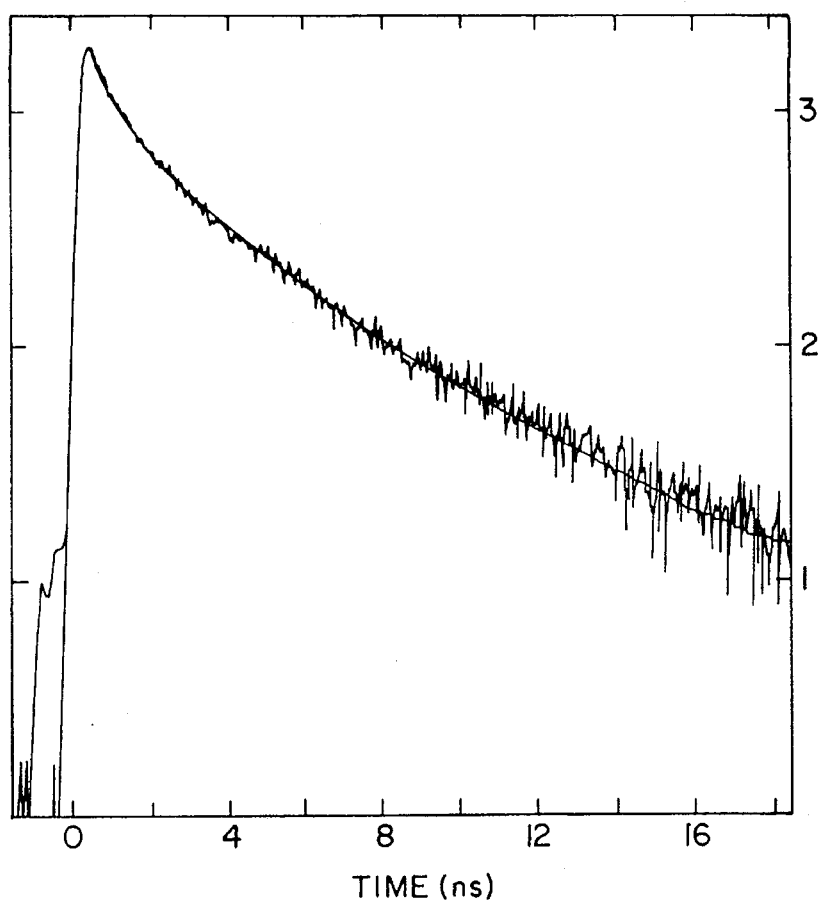
FIG. 11 is a graphical illustration of a fit of the fluorescence decay of human aorta at 305 nm excitation and 350 nm emission.

The fluorescence time decay of human aorta excited in the same range referenced above was measured at 350 and 440 nm, wavelengths at which the emissions of the two fluorophores are well separated. At 305 nm excitation and 350 nm emission, the shorter wavelength fluorophore dominates the fluorescence; at 310 nm excitation and 440 nm emission, the longer wavelength fluorophore should prevail. FIG. 10 shows time decays at 305 and 310 nm excitations. Both decays are similar at the two excitations; however, the 350 nm emission decays somewhat faster than the emission at 440 nm.

Figure 12A:
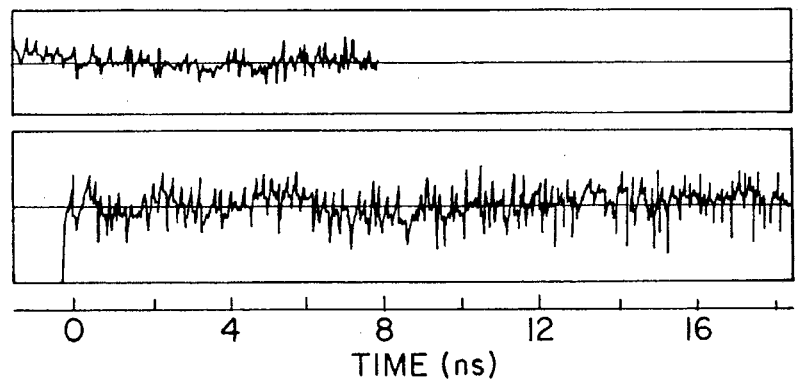
FIGS. 12A and 12B are the autocorrelation of the residuals (±0.3 full scale) and the weighted residuals (±5 full scale) for a three exponential fit ($x^2=1.15$) (at 12A) and the same curves for a four exponential fit ($x^2=1.08$) (at 12B). The residuals for three and four exponentials are similar, however, the autocorrelation for three exponentials shows a long range deviation, indicating a poor fit, while the autocorrelation for four exponentials shows no such deviation, indicating a good fit.
Figure 12B:
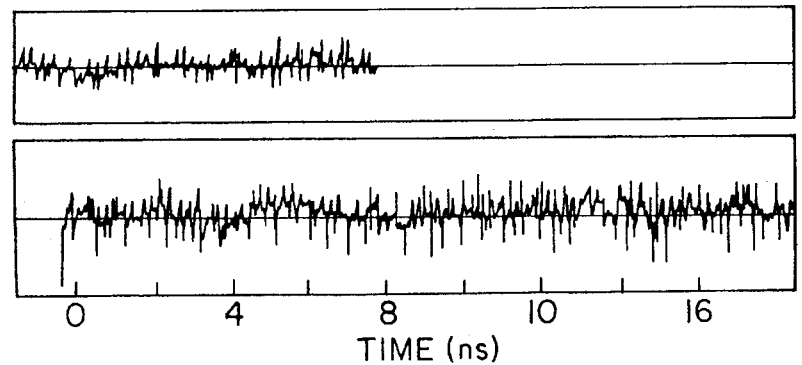

In order to extract information from the time-resolved decays, the decay curves were fit to a sum of exponentials in the form $K(t)=A_1 \exp(-t/\tau_1) + A_2 \exp(-t/\tau_2)+$. Deconvolution analysis was done by an iterative reconvolution method with parameter adjustment by the Marquardt procedure. The quality of the fit was judged by visual inspection of the autocorrelation function of residuals, the weighted residuals, and by $\chi^2$. In our case, the measured decays could not be fit with two or three exponentials, as indicated by the drift in the autocorrelation function (FIG. 12A). A minimum of four exponentials was needed to obtain a good fit (FIG. 12B); an attempt to a fifth exponential did not improve the fit.

The 350 nm emission excited with 305 nm decayed with time constants of 0.003(0.73), 0.65(0.14), 2.1(0.070), and 4.9(0.058). (All time constants $\tau$ are reported in nanoseconds, and their corresponding normalized amplitudes A appear in parentheses.) The 440 nm emission with 310 nm excitation yielded time constants of 0.071(0.52), 0.61(0.29), 2.95(0.14), 8.6(0.052). With both excitations, the last two time constants are longer at 440 nm emission compared with emission at 350 nm. One possible explanation is energy transfer to the longer wavelength fluorophore. A short decay component emerges in both fits; however, with our current experimental resolution (40 ps) and response time (150 ps), we cannot conclude that the values (33 ps and 71 ps) are distinct. Scattered laser light is rejected as a possibility for this fast component, since the cutoff filter eliminates this source of light. A similar short lifetime component has been observed in fluorescence decay of tryptophan in several different proteins, which has been attributed this component to fast energy transfer.

As discussed above, the fluorescence at 350 nm excited by 305 nm is most likely due to tryptophan. Tryptophan fluorescence in solution has two exponentially decaying components with time constants of 0.6 and 2.5 ns. Longer decay constants for tryptophan fluorescence have been observed in other environments. The three long time decay constants of 0.65, 2.1 and 4.9 ns are in the correct range for the known values of tryptophan lifetimes in different environments.

As discussed above, tryptophan is known to be an efficient fluorescing moiety in tissue; in fact it will totally dominate if excited at its absorption peak at 280 nm. However, by carefully choosing the excitation wavelength, about 310 nm, the tryptophan absorption cross-section is much smaller and the emission does not overwhelm much weaker fluorescing chromophores. Therefore, tissues containing relatively more tryptophan (normal vs. plaque) will have more of this efficient chromophore. But efficient fluorescence means that other competing non-radiative depopulating processes are less effective than for weakly emitting chromophores. Since the non-radiative decay processes rather than radiative processes generally dominate the population removal, the excited state for an efficiently emitting chromophore will live longer, yielding a longer fluorescence lifetime. Proportionally higher tryptophan content will lengthen the observed tissue lifetime.

There are other wavelengths of interest: 365 nm excites NAD/NADH; perhaps fluorescence lifetimes will be different in different tissue environment, 400 nm excites blue-emitting chromophores, and 470 nm excites the 500–620 nm chromophores. Similar lifetimes here for the various "peaks" will help confirm the hypothesis of a single fluorescing chromophore which is given structure by hemoglobin reabsorption in mulk tissue. Dissimilar lifetimes would indicate more than one overlapping chromophore emission spectra. Non exponential decays will tend to indicate this also, although one chromophore in two different environment may also be bi-exponential. Changing excitation wavelength may help here; as has already been demonstrated for ultraviolet tissue spectroscopy, the chromophore may be enhanced or inhibited relative to another.

To reiterate, LIF measurements of human artery wall indicate that at least two distinct fluorophores are being excited in aorta in the 305 to 310 nm region. The structural proteins collagen and elastin, via similar cross-linking agents, are probably responsible in large part for the longer wavelength fluorescence. The shorter wavelength fluorescence is attributed to tryptophan.

The present procedure establishes the ability to spectroscopically observe two or more fluorophores and determine relative contributions to the spectrum. The spectral lineshape is very sensitive to excitation wavelengths near the absorption edge. For example, tryptophan shows such sensitivity between 305 and 310 nm, the relative contributions of each fluorophore to the overall spectrum can be precisely controlled. Either fluorophore can be emphasized for study by simply tuning the excitation wavelength a few nanometers; in addition, two or more fluorophores can be simultaneously observed by an appropriate choice of excitation wavelength and the ratio of emitted peaks may be adjusted for optimal comparison. This control is very important in identifying the chromophores and, hence, diagnosing the tissue type and condition for all kinds of bodily tissue. Differences in relative concentrations of the molecules, for instance in normal and diseased arteries, can be spectroscopically monitored; in addition, such relative measurements are both easier to perform and less sensitive to uncertainties in collection efficiency compared to absolute measurements.

LIF spectral signatures of arterial tissues have been observed using ultraviolet excitation. Excitation wavelength is critical to the spectral signatures, and rational choices of the wavelength has a basis in knowledge of the composition of the tissue. Spectral emission can therefore be tailored by selecting the excitation wavelength to enhance differences. Individual tissue components and localized laser damage may be studied microscopically. Spectral "tours" of the thin sections can help determine the individual contributions to the bulk tissue spectra which will help generate a physical and chemical basis for understanding the LIF spectral fingerprint of bulk tissue. Photochemically induced changes in spectra may well be changes in oxidation state of native compounds. Picosecond time resolved measurements will aid in this understanding. This is of general applicability and should be readily adapted for studying cancerous and other diseased and healthy tissue.

Figure 13A:
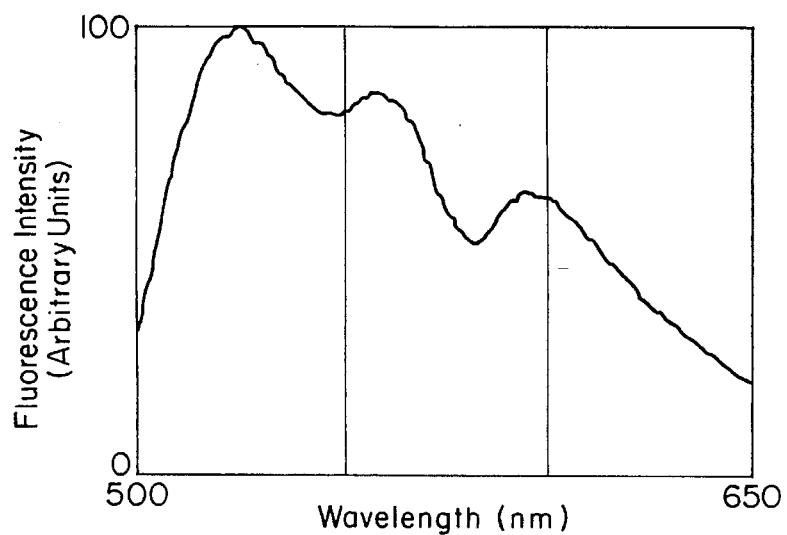
FIGS. 13A, 13B and 13C are schematic graphical representations of the fluorescence spectra of normal tissue, fibrous plaque and fatty plaque respectively.
Figure 13B:
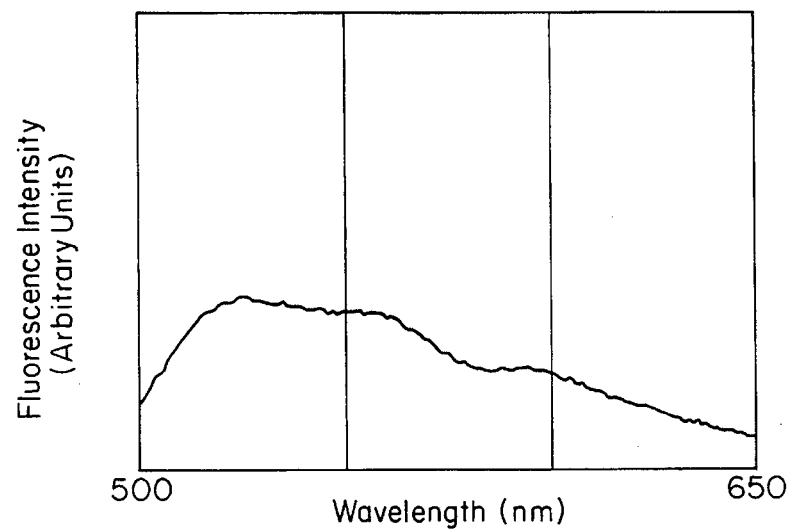
Figure 13C:
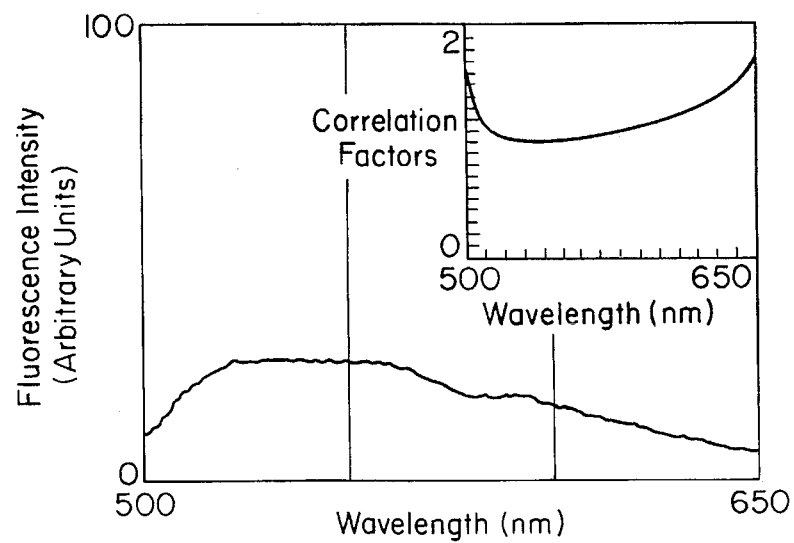
Figure 14A:
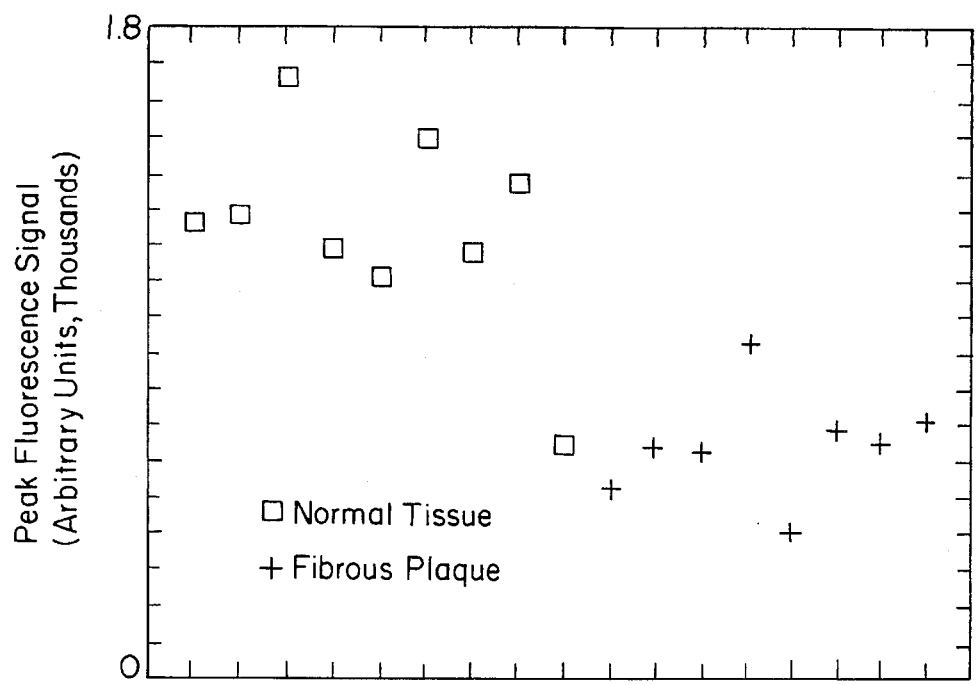
FIGS. 14A and 14B are schematic scatter plots of peak fluorescence and peak to valley ratio (R), respectively, for several normal and fibrous plaque tissue samples.
Figure 14B:
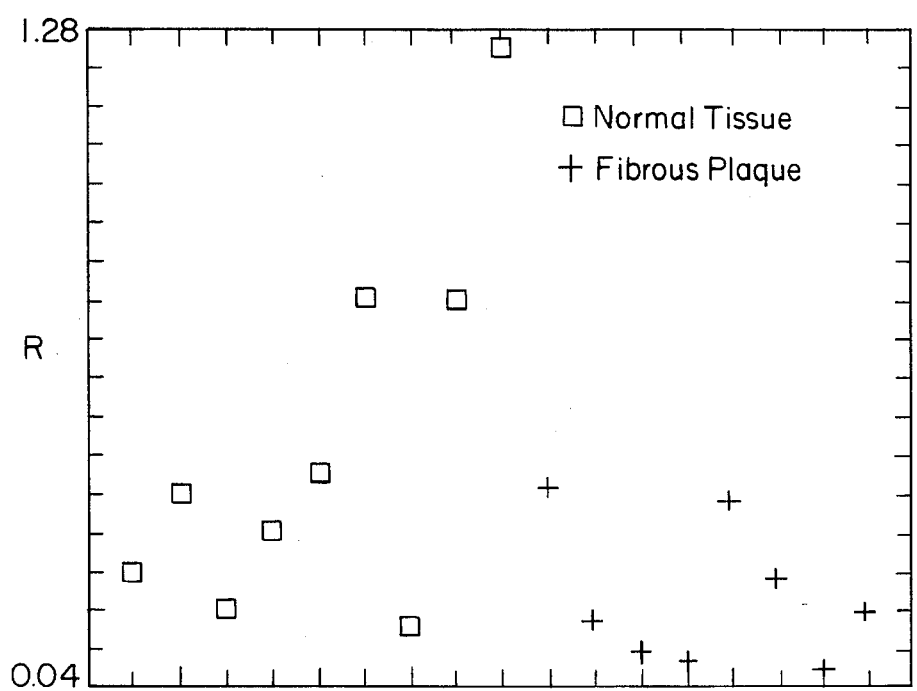

Typical fluorescence spectra for normal aorta, fibrous plaque and fatty plaque obtained with 476 nm excitation (using the apparatus described in Sec. II) are shown in FIG. 13. FIG. 14(b) shows a plot of R, the peak to valley ratio of the fluorescence intensity, for several different samples. Although the average value of R is higher for normal tissue, FIG. 14(b) illustrates that sample-to-sample variability is statistically important and that R is, thus, not a reliable indicator of tissue type. Better discrimination is provided by the peak fluorescence intensity as indicated in FIG. 14(a). These results show that in many cases it is possible to empirically use 476 nm LIF intensity to differentiate human aorta as normal or atherosclerotic. As indicated by the last normal sample, however, this empirical algorithm does not work for all samples.

Tissue fluorescence spectra contain information about the physical and chemical composition of the tissue, and can be deconvoluted to yield this information. Such deconvolution aids in understanding the reasons for sample-to-sample variability in the tissue fluorescence spectra, and predict situations in which sample variability is important. Deconvolution also provides for accuracy in the diagnosis of tissue type. Algorithms have been developed to extract additional information from tissue spectra, such as intimal thickness. The method provides for the determination of the chemical composition of atherosclerotic lesions, providing a method for tracking the development of disease in vivo, and providing important information about both the need to treat and the most effective treatment for a given lesion.

Current methods of diagnosis are incapable of yielding information of this nature. A method of analyzing fluorescence signals from optically thick tissue has been developed which can be used to extract important clinical information about tissue type and chemical composition. Such fluorescence signals are complicated by the interplay of scattering with fluorescence and absorption, thus these effects must be included in a model of tissue fluorescence.

The following model of tissue fluorescence expresses the composite tissue spectrum in terms of contributions from fluorophores, and absorbers which modulate the intrinsic fluorescence spectrum. Scattering is included empirically in the model by describing absorbing species with "attenuation spectra", which include contributions from both absorption and scattering.

An analysis of fluorescence data obtained from a normal and atherosclerotic human artery wall is described below. The date indicates that it is possible to use 476 nm LIF spectroscopy to differentiate human aorta as normal or atherosclerotic, and to determine the chemical constituents responsible for the spectra.

The system used to collect fluorescence spectra from tissue consists of an argon-ion laser, an optical fiber laser catheter, and a scanning monochromator with a photomultiplier tube. One embodiment of an optical fiber laser catheter used to collect data contains seven optical fibers encased in a transparent quartz shield. The central fiber, coupled to the laser, provides a 1 mm diameter spot at the surface of the shield. Six collection fibers, surrounding the central fiber are arranged to view only the tissue illuminated by the central fiber, and are used to collect tissue fluorescence. The distal ends of these fibers are coupled to the entrance slits of the monochromator. The well defined collection geometry of this system represents a substantial improvement over that of typical spectrofluorimeters, in which recorded signals are significantly distorted by reabsorption. FIGS. 13A, 13B and 13C illustrate fluorescence spectra of samples taken in vitro having normal tissue, fibrous plaque and fatty plaque respectively. An excitation intensity of 100 µW/mm$^2$ was used for all spectra. Data was collected at 0.5 nm intervals from 500 to 650 nm; collection time was 40 seconds. Thus, tissue samples were exposed to a fluence of 4 mJ/mm$^2$ per spectrum recorded. This is well below the intensity, 80 mJ/mm$^2$, at which laser-induced alteration of tissue spectral properties become detectable with this system. Spectral resolution of the detector was 6 nm FWHM, and a time constant of 250 msec was used to record all data. Data presented has not been corrected for the non-uniform spectral response of this system. Correction factors are small, however, and are shown in FIG. 13C.

All tissue studied was cadaveric human aorta obtained at autopsy within 24 hours of expiration. Samples were snap frozen in liquid nitrogen and isopentane, and then stored at −70° C. until use. Spectra were obtained from samples kept moist using an isotonic saline solution at room temperature. Tissue was classified as normal, fibrous plaque or fatty plaque under microscopic examination, using standard histologic definitions.

The present model of tissue fluorescence assumes light to traverse the medium in one dimension with exponential attenuation. The wavelength dependent attenuation coefficient includes contributions from both absorption and scattering. Although aortic tissue is composed of three distinct layers (intima, media, adventitia in order of position from the luminal surface), model has assumed that the tissue is a single, optically thick, layer with chromophores distributed uniformly.

The model of a one-layer treatment is correct only when the intimal layer is optically thick. This model is most appropriate for atherosclerotic plaques, in which extensive intimal thickening occurs. It may also be applicable to normal aorta, in cases where substantial diffuse intimal thickening has taken place. In other cases, the composite spectrum will arise from two (or conceivably three) layers; a one layer model will then describe the tissue in terms of some average of its optical properties. The extension to more than one layer is straightforward, but extracting diagnostic information is more complicated.

An understanding of the chromophores responsible for the fluorescence and attenuation properties of tissue is necessary to fully describe the tissue LIF spectra. Studies have demonstrated that composite arterial tissue fluorescence spectra are generated through a combination of intrinsic fluorescence and reabsorption. Using 476 nm laser induced fluorescence microscopy, it has been shown that chromophores in collagen and elastin contribute intrinsic fluorescence in both normal and atherosclerotic tissues. These fluorophores appear to be distributed fairly uniformly throughout individual tissue layers.

In addition, some atherosclerotic tissues contain one or more fluorophore, typically found in necrotic regions, which is contained in ceroid. Ceroid is a morphologic term used to denote substances which stain like a lipid yet are not dissolved by usual lipid solvents, and which fluoresce in the visible when excited by ultraviolet light. Ceroid is a complex of protein associated with oxidized lipids, its exact identity is not known.

Flavins which have broad absorption at 450 nm and broad emission at 540 nm also contribute to the fluorescence. The chromophores also contribute to the composite tissue fluorescence spectrum through reabsorption. A heme containing compound, believed to be oxy-hemoglobin, is also present mainly in the intima of normal aorta, but is found in lesser concentrations in media and atherosclerotic intima as well. The 540 and 580 nm absorption peaks of oxy-hemoglobin produce the valleys at 540 and 580 nm in the composite tissue fluorescence spectra. FIG. 14(b) indicates that the concentration of oxy-hemoglobin varies widely from sample to sample.

In principle, all tissue components absorb some light in this spectral region, however, the fluorescence spectra of normal and fibrous plaques (which do not have extensive necrotic regions), can be based on the analysis of three sets of spectra, namely those originating from the fluorophores in collagen and elastin and the absorption spectrum of oxy-hemoglobin. With these assumptions, the following equation describes the composite tissue fluorescence spectrum.

$$S(\lambda) = \int_0^\infty kI_o e^{-(C_F \epsilon_{Fo} + C_A \epsilon_{Ao})z} \beta L(\lambda) e^{-(C_F \epsilon_F(\lambda) + C_A \epsilon_A(\lambda))z} dz \quad (1)$$

In Eq. (1), $S(\lambda)$ is the detected tissue fluorescence power; $I_o$ is the incident laser power. k is a factor which accounts for backscattered light that augments the incident $I_o$. Here, we assume k=1. The first exponential term in the integral represents the attenuation of the incident 476 nm light, as the beam traverses the tissue. $\beta L(\lambda)$ describes the conversion of absorbed excitation light into fluorescence. The final exponential term gives the attenuation of the emitted light as it returns through the tissue to the detector. Performing the integration over the thickness of the tissue, z, yields $$S(\lambda) = \frac{kI_0 \beta L(\lambda)}{F(\lambda) + xA(\lambda)} \quad (2)$$

Where $$F(\lambda) = C_F(\epsilon_{Fo} + \epsilon_F(\lambda)) \quad (3)$$

$$xA(\lambda) = C_A(\epsilon_{Ao} + \epsilon_A(\lambda)) \quad (4)$$

In Eq. (2), $L(\lambda)$ represents a dimensionless, normalized fluorescence lineshape function for collagen (elastin and chromophores). $\beta$ is given by the product of the collagen (elastin and chromophores) concentration, the quantum efficiency, the molar absorption coefficient at the incident wavelength, and the collection efficiency of the detection system. Thus, $\beta$ has units of inverse length. $F(\lambda)$ and $xA(\lambda)$, with units of inverse length, represent the attenuation spectra for chromophores of collagen, elastin and oxy-hemoglobin respectively (Eqs. (3) and (4), where C and $\epsilon$ are the chromophore concentration and molar attenuation coefficient (length$^{-1}$)respectively). These bandshapes include attenuation of both the excitation ($\epsilon_o$) and emitted light ($\epsilon(\lambda)$) in the tissue. Equation (3) holds only if absorption of tissue components other than hemoglobin is small compared to that of collagen (elastin and chromophores).

The attenuation spectrum of oxy-hemoglobin is written as $xA(\lambda)$ to include the varying concentration of this chromophore. In this description, $A(\lambda)$ is a constant lineshape which is proportional to the molar attenuation coefficient, but is normalized to one. x is linearly related to the concentration of oxy-hemoglobin in the tissue. This treatment is not necessary for $F(\lambda)$, assuming that the concentration of collagen (elastin and chromophores) does not vary widely from sample to sample.

Figure 15:
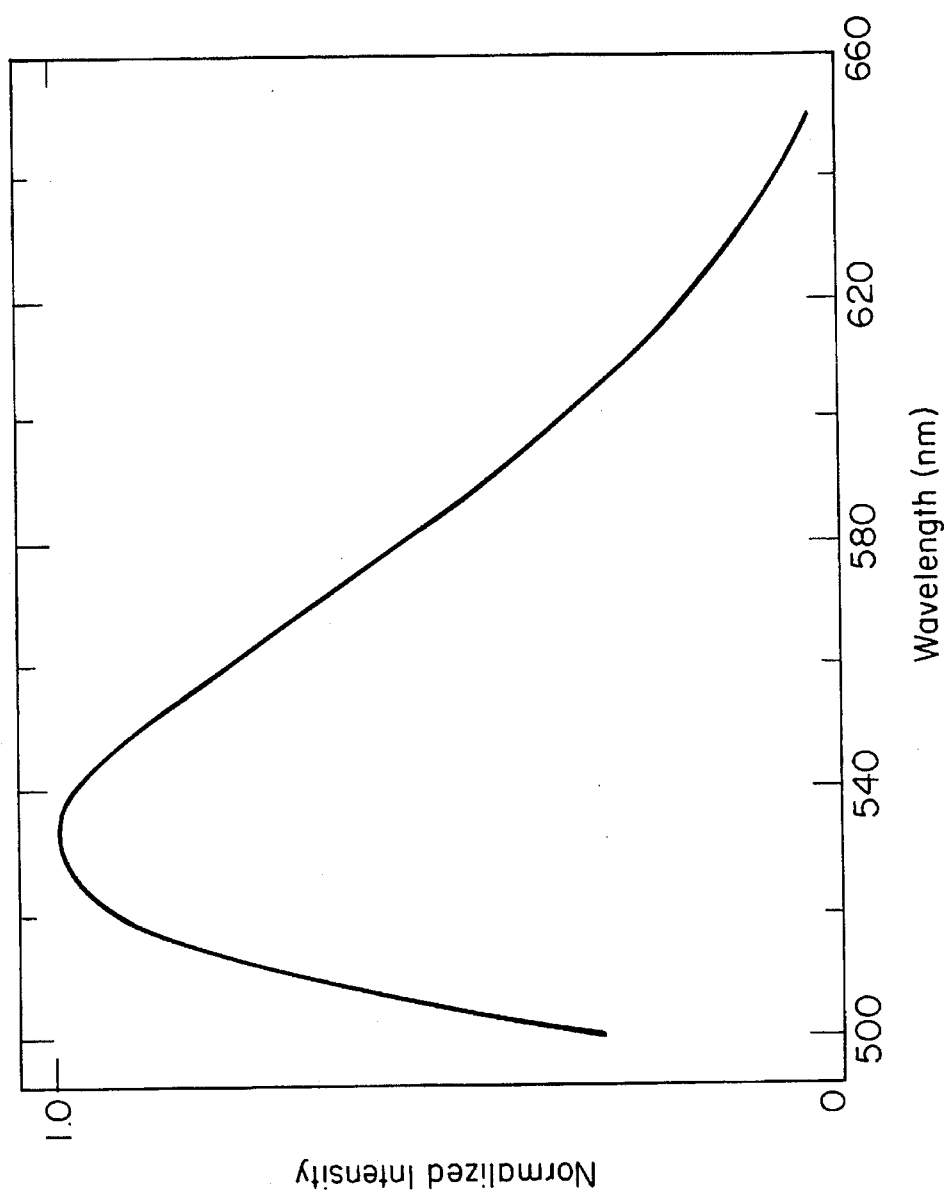
FIG. 15 is a schematic graphical illustration of L($\lambda$), the normalized fluorescence lineshape of collagen.

In order to fix the lineshapes described in Eq. (2) and determine the ultimate accuracy with which this model could represent tissue fluorescence spectra, data was first analyzed from a simple tissue system. An optically thick section of normal media was blunt dissected from a sample of normal aorta to provide a tissue sample which truly consisted of one layer. A fluorescence spectrum was obtained from a 10 μm frozen section of media, providing unattenuated emission. In this case, $S(\lambda)$ is given by $I_o \beta L(\lambda) \delta z$, where δz is the sample thickness. Thus, $\beta L(\lambda)$ for media (FIG. 15) can be determined by simply dividing $S(\lambda)$ by the sample thickness.

Figure 16A:
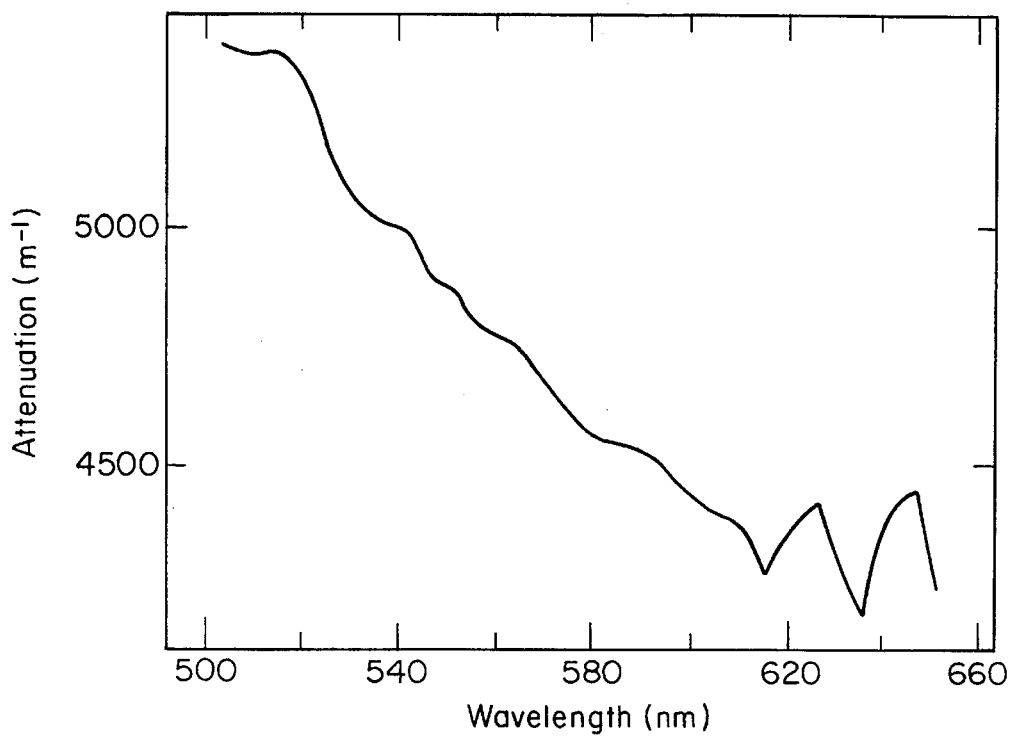
FIGS. 16A and 16B are schematic graphical illustrations of the fitted attenuation spectrum of collagen and oxyhemoglobin respectively.
Figure 16B:
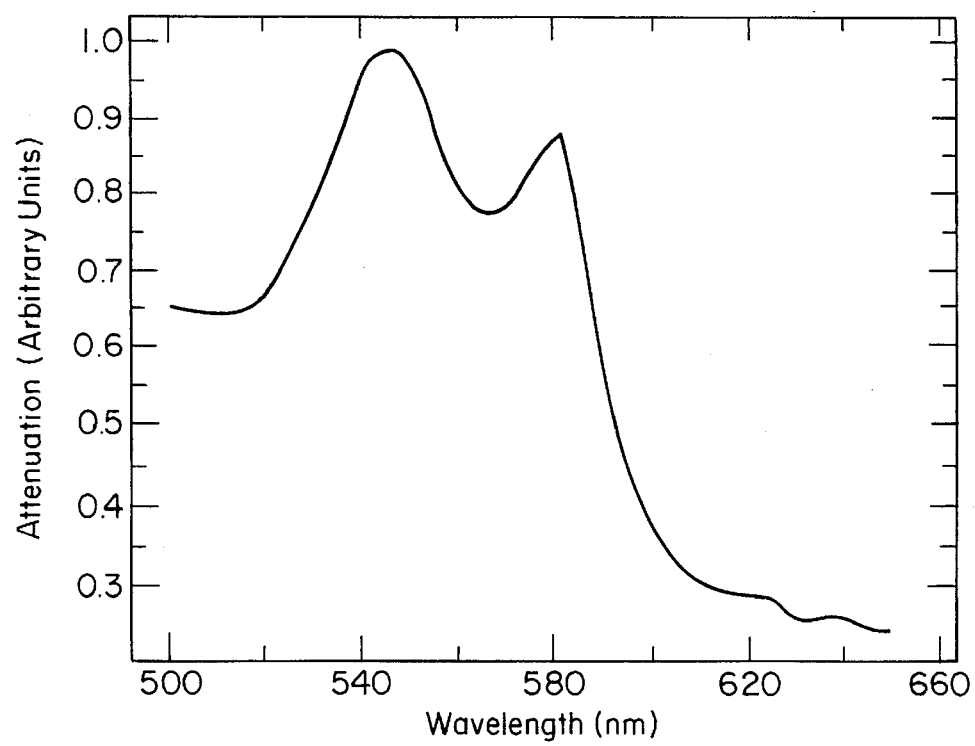

A fluorescence spectrum was obtained from bulk media with zero hemoglobin concentration, x=0(Eq. (1)), thus yielding $F(\lambda)$, FIG. 16(a), directly. The bulk media was then exposed to a solution containing free oxy-hemoglobin (hemolyzed human blood with EDTA) for controlled periods of time in order to determine $xA(\lambda)$. With increasing times of exposure, the value of x was observed to increase, consistent with our previous observation that the oxy-hemoglobin content of tissue can be increased by exposing tissue to free oxy-hemoglobin. An $A(\lambda)$ lineshape, FIG. 16(b), was determined for several concentrations of hemoglobin and averaged. The maximum concentration of oxy-hemoglobin studied corresponded roughly to the maximum concentration seen in typical in vitro tissue samples.

Having elucidated the lineshapes in Eq. (2), the model was then used to fit fluorescence spectra obtained from both normal and diseased arterial tissue. In vitro fluorescence spectra of normal and atherosclerotic tissue corresponding to the samples displayed in FIG. 14 were digitized every 5 nm in preparation for numerical analysis. A Levenberg-Marquardt algorithm was used to fit the adjustable parameters of the model, $\beta$ and x, by minimizing the sum of the squares of the differences between the calculated and experimental spectra.

FIG. 16 compares several of the calculated and experimentally measured tissue fluorescence spectra. It was found that all of the normal tissue spectra could be fit to Eq. (2). About half of the fibrous plaque spectra could also be fit to the model described by Eq. (2); however, a mismatch was found in the region between 530 and 560 nm for the remaining fibrous plaque samples. Although not presented here, similar complications were found in fitting spectra of fatty plaque tissues. This indicates the presence of an additional chromophore in some of the fatty and fibrous samples, likely to be those contained in ceroid.

Figure 17A:
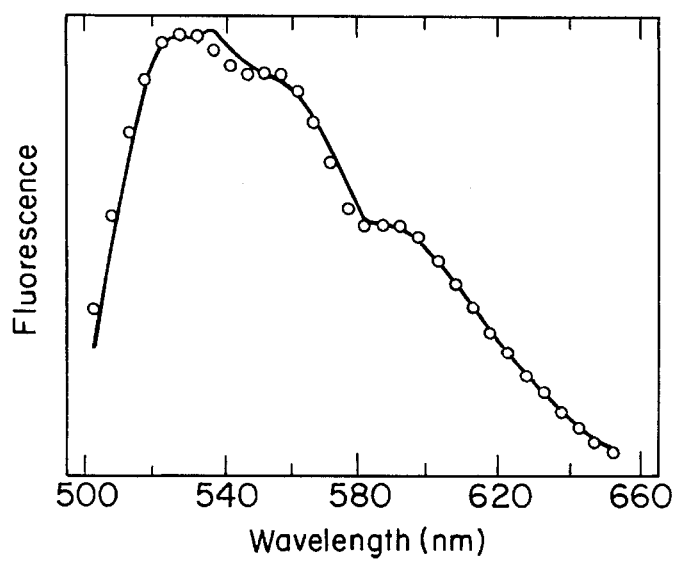
FIGS. 17A, 17B and 17C are graphical illustrations comparing experimentally measured data with the calculated fluorescence spectra (solid curves) of normal tissue (17A) and fibrous plaque (17B and 17C).
Figure 17B:
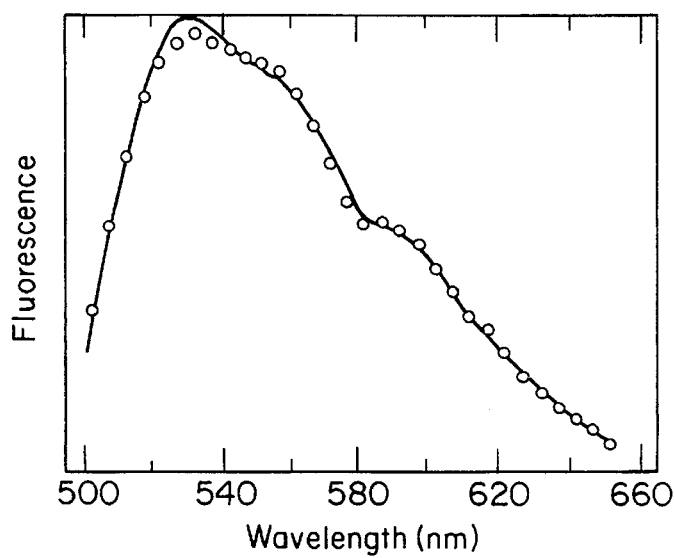
Figure 17C:
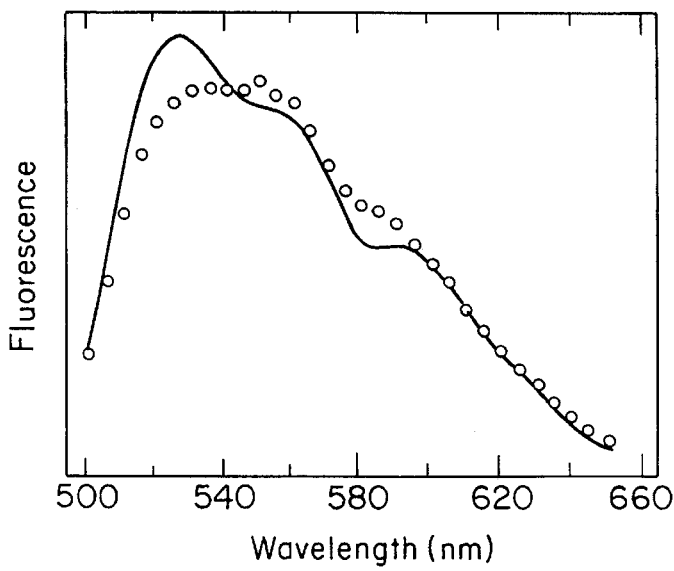
Figure 18A:
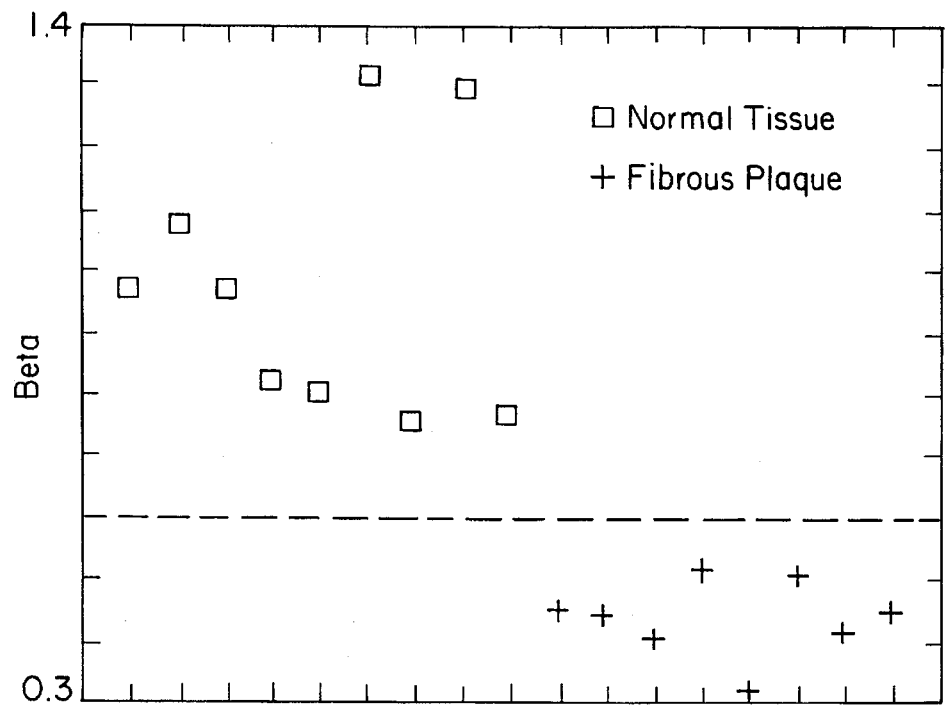
FIGS. 18A and 18B are schematic scatter plots of the same data presented in FIG. 14 in which $\beta$ (18A) and $\chi$ (18B) are plotted.
Figure 18B:
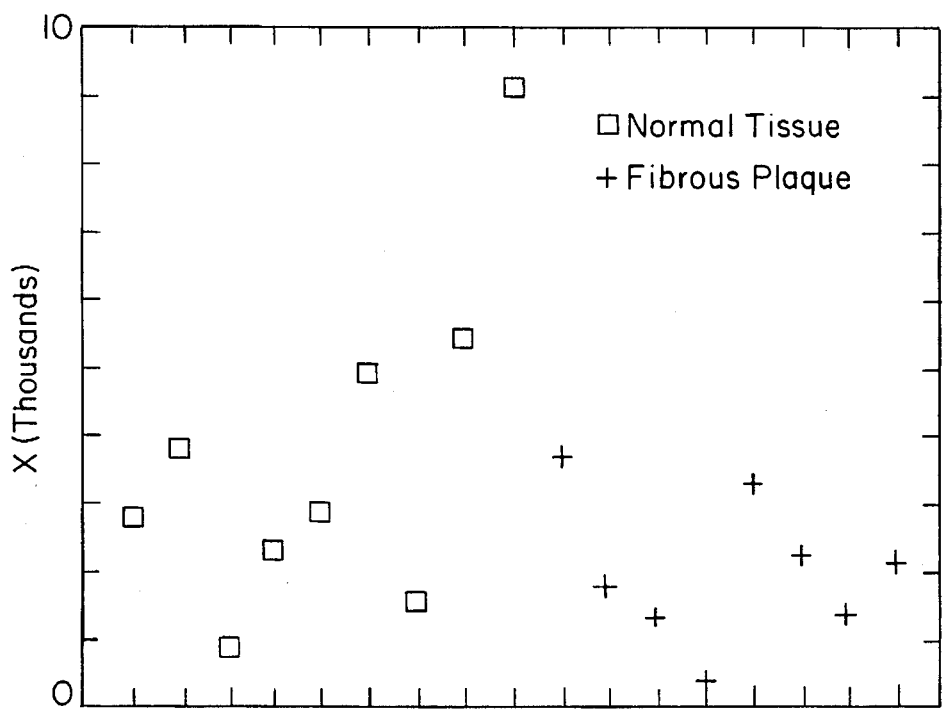

FIG. 17 shows the calculated values of $\beta$ and x for each tissue sample presented in FIG. 2. The $\beta$ values are able to discriminate diseased from normal tissue better than the empirical LIF intensities, as indicated by the dashed line in FIG. 17. Note especially that the last normal sample, which was diagnosed incorrectly using the directly measured 476 nm LIF intensity, is diagnosed correctly using $\beta$. This is due to the fact that the model of tissue fluorescence separates the effects of fluorescence and reabsorption while the directly measured method does not. Since this sample had a high concentration of oxy-hemoglobin (high values of R, x) its peak fluorescence intensity was reduced, yielding an incorrect diagnosis. The model, however, separates these effects so that $\beta$ provides a better indicator of sample type.

In addition, $\beta$ provides a chemical basis for understanding the extent of disease. A lower $\beta$ can be due to a higher ratio of collagen to elastin, which is consistent with the structural changes that occur in the intima as atherosclerosis develops. Changes in the value of $\beta$ can also be related to alterations in the structural proteins of the aorta which modify the environment or concentration of the fluorophores. The average value of x is higher for normal tissue, indicating a higher average concentration of oxy-hemoglobin. However, the value of x varied widely from sample to sample. This is consistent with the observations made in FIG. 14(b). The correlation between the relative values of x (FIG. 14(b)) and R is striking.

The experiments and calculations presented here suggest an important reason for the sample-to-sample variability observed in R and x, in cadaveric artery samples. In general, tissue samples obtained from cadavers will be exposed for varying periods of time to varying concentrations of free hemoglobin as red blood cells lyse. Thus, cadaveric tissues will contain varying amounts of oxy-hemoglobin. The higher average content of oxy-hemoglobin in normal tissues is consistent with our observation that hemoglobin is taken up most readily in the intima of normal tissues, and less readily in the intima of atherosclerotic tissues. Hence, earlier work utilizing 480 nm laser induced fluorescence yielded data that was a reflection of this trend.

When tissues are exposed to whole blood, where hemoglobin is contained in red blood cells, the tissue oxy-hemoglobin content is unaffected. This suggests that there may be an important difference in the amount of oxy-hemoglobin in tissues studied in vivo and in vitro. The present studies show that normal artery wall in vivo does not contain oxy-hemoglobin, but this absorber may be present in vivo in various pathologic conditions, for example hemorrhagic plaques. Thus, the model represents an important connection between data obtained in vivo and in vitro. It can be used to simulate the effect of different oxy-hemoglobin concentrations in a given tissue sample.

A simple model of tissue fluorescence can be utilized to describe the fluorescence spectra of optically thick tissue samples. As shown with the emission spectra of artery wall, the model can be used to separate effects due to fluorescence and absorption. In addition, contributions from individual chromophores can be deconvoluted and their relative concentrations can be extracted. This information can be utilized to diagnose tissue type more accurately than empirical algorithms, and may potentially prove to be useful in determining the chemical composition of atherosclerotic lesions in vivo.

Note several of the assumptions made in writing Eq. (1). First, the application of a one layer model to describe normal tissue fluorescence. The measured intimal thickness of the normal tissue samples were less than the 1/e penetration depth at 476 nm. In applying a one layer model to a two layer system we calculate some average value of $\beta$ and x. These average values can vary, ranging from $\beta$ or x of layer two to that of layer one as the intimal thickness increases.

Secondly, the model assumes a simple fluorophore, emission profile from collagen (elastin). However, data from several fibrous plaque samples could not be fit to Eq. (1) indicating the presence of additional chromophores, likely including the flavin group. Finally, our treatment incorporates the interplay of scattering and absorption empirically through exponential attenuation spectra, $F(\lambda)$ and $A(\lambda)$. The results from this approximation produce calculated attenuation spectra of chromophores in collagen (elastin) and hemoglobin that are similar in shape, but not identical to measured absorption spectra. The present method provides a technique for comparing attenuation and absorption spectra, thus determining the relative importance of scattering.

The model can be extended to include the layered structure of tissue and additional chromophores. In addition, independent measures of tissue fluorescence efficiency and oxy-hemoglobin concentration can be obtained in order to correlate these values to those calculated in the model.

We claim:

1. A method of measuring chromophores to identify tissue composition comprising;

selecting a range of wavelengths which includes known excitation wavelengths of plurality of chromophores at which each chromophore undergoes fluorescence;

irradiating endogenous tissue with radiation having at least one wavelength within the range for each chromophore;

detecting a fluorescence emission spectrum of the tissue resulting from the irradiation thereof;

deconvolving the spectrum to determine the relative contribution of each fluorescing chromophore to the detected spectrum;

separating a component of the spectrum resulting from reabsorption by the tissue to provide an adjusted spectrum; and identifying at least one chromophore in the tissue from the adjusted spectrum.

2. The method of measuring chromophores of claim 1 further comprising the step of determining the wavelength of peak fluorescence of each chromophore.

3. The method of claim 2 further comprising the step of determining the ratio of two selected fluorescence peaks.

4. The method of targeting chromophores of claim 1 further comprising separating a further component of the spectrum resulting from reabsorption by the tissue.

5. The method of measuring chromophores of claim 1 wherein the tissue comprises arterial tissue.

6. The method of measuring chromophores of claim 1 wherein the chromophore comprises ceroid.

7. A method of measuring chromophores to identify arterial tissue composition comprising;

selecting a range of wavelengths which includes known excitation wavelengths of plurality of chromophores at which each chromophore undergoes fluorescence;

irradiating endogenous arterial tissue with radiation having at least one wavelength within the range for each chromophore;

detecting a fluorescence emission spectrum of the tissue resulting from the irradiation thereof;

deconvolving the spectrum to determine the relative contribution of each fluorescing chromophore to the detected spectrum;

separating a component of detected the spectrum resulting from reabsorption by the tissue from the detected spectrum to provide an adjusted spectrum; and identifying at least one chromophore in the tissue from the adjusted spectrum.

8. The method of measuring chromophores of claim 7 further comprising separating a further component of the spectrum resulting from reabsorption by the tissue.

9. A method of measuring chromophores to identify tissue composition comprising;

selecting a range of wavelengths which includes known excitation wavelengths of plurality of chromophores at which each chromophore undergoes fluorescence;

irradiating endogenous tissue with radiation having at least one wavelength within the range for each chromophore;

detecting a fluorescence emission spectrum of the tissue resulting from the irradiation thereof;

deconvolving the spectrum to determine the relative contribution of each fluorescing chromophore to the detected spectrum;

separating a component of the spectrum resulting from reabsorption by the tissue to provide an adjusted spectrum; and identifying at least one chromophore in the tissue from the adjusted spectrum relative to a reference spectrum.

10. The method of measuring chromophores of claim 9 further comprising separating a further component of the spectrum resulting from reabsorption by the tissue.

11. The method of claim 9 further comprising the step of determining the wavelength of peak fluorescence of each chromophore.

12. A method of measuring chromophores to identify tissue composition comprising;

irradiating endogenous tissue with radiation having at least one wavelength for excitation of a chromophore within the tissue;

detecting a fluorescence emission spectrum of the tissue resulting from the irradiation thereof;

deconvolving the spectrum to determine the relative contribution of a fluorescing chromophore within the detected spectrum;

separating a component of the spectrum resulting from reabsorption by the tissue to provide an adjusted spectrum; and identifying at least one chromophore in the tissue from the adjusted spectrum.

13. The method of measuring chromophores of claim 12 further comprising the step of determining the wavelength of peak fluorescence of each chromophore.

14. The method of claim 13 further comprising the step of determining the ratio of two selected fluorescence peaks.

15. The method of measuring chromophores of claim 12 further comprising separating a further component of the spectrum resulting from reabsorption by the tissue.

16. The method of measuring chromophores of claim 12 further comprising irradiating the tissue with laser radiation.

* * * * *